United States Patent
Barta et al.

(10) Patent No.: US 7,064,147 B2
(45) Date of Patent: Jun. 20, 2006

(54) AMINO ACIDS WITH AFFINITY FOR THE α-2-DELTA-PROTEIN

(75) Inventors: Nancy Sue Barta, Brighton, MI (US); Jacob Bradley Schwarz, Ann Arbor, MI (US); Andrew John Thorpe, Whitmore Lake, MI (US); David Juergen Wustrow, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 80 days.

(21) Appl. No.: 10/401,060

(22) Filed: Mar. 27, 2003

(65) Prior Publication Data

US 2003/0195251 A1    Oct. 16, 2003

Related U.S. Application Data

(60) Provisional application No. 60/368,413, filed on Mar. 28, 2002.

(51) Int. Cl.
*A61K 31/195* (2006.01)
*C07C 229/00* (2006.01)

(52) U.S. Cl. ..................................... 514/561; 562/553
(58) Field of Classification Search ................ 514/557, 514/570, 561; 562/553, 562
See application file for complete search history.

(56) References Cited

U.S. PATENT DOCUMENTS

| | | | |
|---|---|---|---|
| 5,344,957 A | 9/1994 | Bovy et al. | |
| 5,578,606 A * | 11/1996 | Vazquez et al. | ............ 514/314 |
| 5,614,498 A | 3/1997 | Ishikawa et al. | |
| 5,840,961 A | 11/1998 | Behling et al. | |
| 6,011,066 A | 1/2000 | Wang | |
| 6,121,325 A | 9/2000 | Chen et al. | |
| 6,306,909 B1 | 10/2001 | Weaver et al. | |

FOREIGN PATENT DOCUMENTS

| | | |
|---|---|---|
| EP | 0 561 758 | 9/1993 |
| EP | 0 678 788 | 10/1995 |
| EP | 1 013 769 | 6/2000 |
| FR | 1 377 7366 | 12/1963 |
| GB | 2 323 594 | 9/1998 |
| WO | WO 91/09840 | 7/1991 |
| WO | WO 95/15684 | 6/1995 |
| WO | WO 98/17627 | 4/1998 |
| WO | WO 40055 | 9/1998 |
| WO | WO 98/56234 | 12/1998 |
| WO | WO 00/76958 | 12/2000 |
| WO | WO 01/87821 | 11/2001 |
| WO | WO 01/88101 | 11/2001 |
| WO | WO 02/22568 | 3/2002 |
| WO | WO 02/30871 | 4/2002 |

OTHER PUBLICATIONS

Griffinth et al, Liquid Chromatographic Separtion of Enantiomes of Beta -amino acids using a chiral stionary phase, Mar. 1986, J. of Chromatography, 362(3), p. 345-352.*

Juaristi et al , Enantioselective Synthesis of beta-amino acids. 1996, Tetrahedron:Asymmetry, vol. 7, No. 8, p. 2233-2246.*

Palomino E., "Delivery of Drugs Through Dihydropyridine Carriers", Drugs of the Future, (1990), pp. 361-368, vol. 15(4).

Juaristi, E., "Enantioselective Synthesis of beta-Amino Acids", Tetrahedron: Asymmetry, (1996) pp. 2233-2246, vol. 7, No. 8.

Lazar, L. et al, "A Simple Synthesis of Beta-Alkyl-Substituted Beta-Amino Acids", Synth. Commun., (1998), pp. 219-224, vol. 28(2).

Davies, S.G. et al, "Asymmetric Synthesis of Beta-Phenylalanine, Alpha-Methyl-Beta-Phenylalanines and Derivatives", J. Chem. Soc., Chem. Commun., (1993), pp. 1153-1155.

Davies, S. G., et al, "A Succinct Asymmetric Synthesis of (2S,3R)-2-Methyl-3-aminopentanoic Acid Hydrochloride", SYNLETT, (1994), pp. 117-118.

Ishikawa et al, "Chiral Lewis Acid-Hydroxylamine Hybrid Reagent for Enantioselective Michael Addition Reaction Directed Towards Beta-Amino Acids Synthesis", SYNLETT, (1998), pp. 1291-1293, vol. 11.

Hawkins J. et al., Asymmetric Michael Reactions of 3,5-Dihydro-4H-dinaphth[2,1-c:1',2'-e]azepine with Methyl Crotonate, J.Org.Chem., (1986), pp. 2820-2822, vol. 51.

Bull S.D. et al, "Asymmetric Synthesis of Beta-amino Acid Scaffolds", J. Chem. Soc., Perkin Trans. 1, (2001), pp. 2931-2938, vol. 22.

Evans, D. A. et al, "A General Method for the Synthesis of Enantionmerically Pure Beta-Substituted, Beta-Amino Acids through Alpha-Substituted Succinic Acid Derivatives", J. Org. Chem., (1999), pp. 6411-6417, vol. 64.

Sibi, M.P. et al., "A New Methodology for the Synthesis of Beta-Amino Acids", J. Chem. Soc., Perkin Trans. I, (2000), pp. 1461-1466, vol. 9.

Arvanitis et al., Enantioselective synthesis of 2-substitured 3-amniopropanoic acid (Beta-alanine) derivatives which are Beta-analogues of aromatic amino acids, J. Chem. Soc., Perkin Trans. 1, (1998), pp. 521-528.

Yuen P. W. et al, "Enantioselective Synthesis of PD144723: A Potent Stereospecific Anticonvulsant", Bioorganic & Med. Chem Lett., (1994), pp. 823-825, vol. 4(6).

(Continued)

Primary Examiner—Cecilia J. Tsang
Assistant Examiner—Taylor Victor Oh
(74) Attorney, Agent, or Firm—Karen DeBenedictis; Matthew J. Russo; Charles W. Ashbrook

(57) ABSTRACT

This invention relates to certain β-amino acids that bind to the alpha-2-delta (α2δ) subunit of a calcium channel. These compounds and their pharmaceutically acceptable salts are useful in the treatment of a variety of psychiatric, pain and other disorders.

8 Claims, No Drawings

OTHER PUBLICATIONS

Ho, G.J. et al, "Lithium-Initiated Imide Formation. A Simple Method for N-Acylation of 2-Oxazolidinones and Bornane-2, 1—Sultam", J. Org. Chem., (1995), pp. 2271-2273, vol. 60.

Seebach, D. et al, "EPC__Synthesis of Beta-Amino Acid Derivatives through Lithiated Hydropyrimidines" EUR: J. Org. Chem., (1999), pp. 335-360.

Paine, J.B. et al, "Pyrrole Chemistry. The Cyanovinyl Aldehyde Protecting Groups", J. Org. Chem., (1976), pp. 2826-2835, vol. 41, No. 17.

Tang, T. P. et al, "The tert-Butanesulfinyl Group: An Ideal Chiral Directing Group and Boc-Surrogate for the Asymmetric Synthesis and Applications of Beta-Amino Acids", J. Org. Chem., (1999), pp. 12-13, vol. 64.

Gee, N. S. et al, "The Novel Anticonvulsant Drug, Gabapentin (Neurontin), Binds to the Alpha2Beta Subunit of a Calcium Channel", J. Biol. Chem., (1996), pp. 5768-5776, vol. 271(10).

Sluka, K., et al, "Unilateral Intramuscular Injections of Acidic Saline Produce a Bilateral Long-Lasting Hyperalgesia", Muscle Nerve, (2001), pp. 37-46, vol. 24.

Dixon, W., "Efficient Analysis of Experimental Observations", Ann. Rev. Pharmacol. Toxicol., (1980), pp. 441-462, vol. 20.

Randall L.O., et al, "A Method for Measurement of Analgesic Activity On Inflamed Tissue", Arch. Int. Pharmacodyn., (1957), pp. 409-419, vol. 4.

Hargreaves, K. et al, "A New and Sensitive Method for Measuring Thermal Nociception in Cutaneous Hyperalgesia", PAIN, (1988), pp. 77-88, vol. 32.

Vogel, J.R. et al, "A Simple and Reliable Conflict Proceure for Testing Anti-Anxiety Agents", PSYCHOPHARMACOLOGIA, (1971), pp. 1-7, vol. 21.

Liang, J. et al, "Synthesis of Unit A of Cryptophycin via a [2,3]-Wittig Rearrangement", J. Org. Chem., (1999), pp. 1459-1463, vol. 64.

Hill, R. K. et al., "Asymmetric Induction in the Thermal Reactions of Allylic Alcohols with N, N-Dimethylacetamide Dimethyl Acetal and Triethyl Acetal and Triethyl Orthoacetate", J. Org. Chem., (1972), pp. 3737-3740. vol. 37. No. 23.

Gerwick, W. et al., "Total Structure of Hormothamnin A, A Toxic Cyclic Undecapeptide From the Tropical Marine Cyanobacterium Hormothamnion Enteromorphoides", TETRAHEDRON, (1992). pp. 2313-2324. vol. 48. No. 12.

Jefford, C. et al., "An Enantiospecific Synthesis of Beta-Amino Acids", Tetrahedron Letters, (1993), pp. 1111-1114, vol. 34, No. 7.

Gol'dfarb, Y.L. et al., "Synthesis of Aliphatic Amino Acids from Thiophene Derivatives", Chemical Abstracts, p. 12837, Col. 2, vol. 28 (Abstract Only).

Rodionov, V.M., "The Hoffmann reaction. III. Reaction of Acylated Amides of Beta-Aminopelagonic Acid with Alkaline Hypobromites", Chemical Abstracts, (1951), p. 8453, Col. 1. vol. 45. No. 19 (Abstract Only).

Borodina, G.M., "Synthesis of Some Derivatives of Aliphatic Beta-Amino Acids", Chemical Abstracts, (1955), p. 12291, Col. 1, vol. 49, No. 18 (Abstract Only).

Rodionov, V. M., et al., "Synthesis and Separation of Diastereoisomeric Gamma-Ethyl-Beta-Aminocaprylic Acids and Their Derivatives", Chemical Abstracts, (1956). vol. 50. No. 20 (Abstract Only).

Slopianka, M. et al., "Thiocaronyl Olefination", Chemical Abstracts, (1981), vol. 96, No. 13 (Abstract Only).

Griffith, O.W. et al., "Liquid Chromatographic Separation of Enantiomers of Beta-Amino Acids Using a Chiral Stationary Phase", Chemical Abstractsm, (1986), vol. 105, No. 21, (Abstract Only).

Database Crossfire Beilstein, Beilstein Institut Zur Foerderung Der Chenischen Wissenchaften, Frankfurt Am Main, DE Database Accession no. 1723420 (BRN), XP002242310 & Zh. Obshch. Khim, vol. 26, (1956), p. 793, 796.

Lazar, L., et al., "A Simple Synthesis of Beta-Alkyl-Substituted Beta-Amino Acids", Synth. Commun., (1998), vol. 28(2), pp. 219-224.

Baskakov, Y. A. et al., "Preparation of the Cyclic Hydrazide of Maleic Acid and of Some of its Derivatives", Database Crossfire Beilstein, Beilstein Institut Zur Foerderund Der Chenischen Wissenschaften, Frankfurt Am Main, DE Database Accession No. 1770439 (BRN), XP002242312.

Vara Prasad, J. V. N., "2.2'-Dithiobisbenzamides Derived from Alpha-, Beta- and Gamma-Amino Acids Possessing Anti-HIV Activities: synthesis and Structure-Activity Relationship", Bioorganic 7 Meicinal Chemistry, (1998), pp. 1707-1730.

PCT Internation Search Report PCT/IB03/00976.

* cited by examiner

AMINO ACIDS WITH AFFINITY FOR THE α-2-DELTA-PROTEIN

This application claims the benefit of U.S. Provisional Application No. 60/368,413 filed Mar. 28, 2002.

BACKGROUND OF THE INVENTION

This invention relates to certain β-amino acids that bind to the alpha-2-delta (α2δ) subunit of a calcium channel. These compounds and their pharmaceutically acceptable salts are useful in the treatment of a variety of psychiatric, pain and other disorders.

SUMMARY OF THE INVENTION

This invention relates to compounds of the formula I

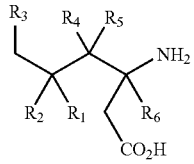

wherein $R_1$ is hydrogen or $(C_1–C_6)$alkyl optionally substituted with from one to five fluorine atoms;

$R_2$ is hydrogen or $(C_1–C_6)$alkyl optionally substituted with from one to five fluorine atoms; or $R_1$ and $R_2$, together with the carbon to which they are attached, form a three to six membered cycloalkyl ring;

$R_3$ is $(C_1–C_6)$alkyl, $(C_3–C_6)$cycloalkyl, $(C_3–C_6)$cycloalkyl-$(C_1–C_3)$alkyl, phenyl, phenyl-$(C_1–C_3)$alkyl, pyridyl, pyridyl-$(C_1–C_3)$alkyl, phenyl-N(H)—, or pyridyl-N(H)—, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-$(C_1–C_3)$alkyl and said pyridyl-$(C_1–C_3)$alkyl, respectively, can be optionally substituted with from one to three substituents, preferably with from zero to two substituents, independently selected from chloro, fluoro, amino, nitro, cyano, $(C_1–C_3)$alkylamino, $(C_1–C_3)$alkyl optionally substituted with from one to three fluorine atoms and $(C_1–C_3)$alkoxy optionally substituted with from one to three fluorine atoms;

$R_4$ is hydrogen or $(C_1–C_6)$alkyl optionally substituted with from one to five fluorine atoms;

$R_5$ is hydrogen or $(C_1–C_6)$alkyl optionally substituted with from one to five fluorine atoms; and $R_6$ is hydrogen or $(C_1–C_6)$alkyl;

and the pharmaceutically acceptable salts of such compounds.

Specific embodiments of this invention include the following compounds of the formula I and their pharmaceutically acceptable salts:

3-Amino-5,8-dimethyl-nonanoic acid;
3-Amino-5,5,7-trimethyl-octanoic acid;
3-Amino-5,5,8-trimethyl-nonanoic acid;
3-Amino-5,5,6-trimethyl-heptanoic acid;
(3S,5S)-3-Amino-5,8-dimethyl-nonanoic acid;
(3S,5R)-3-Amino-5,8-dimethyl-nonanoic acid;
(3S)-3-Amino-5,5,6-trimethyl-heptanoic acid;
(3S)-3-Amino-5,5,7-trimethyl-octanoic acid;
(3S)-3-Amino-5,5,8-trimethyl-nonanoic acid; and
(3S)-3-Amino-5,5,9-trimethyl-decanoic acid.

Other examples of specific embodiments of this invention are the following compounds of the formula I and their pharmaceutically acceptable salts:

3-Amino-6-cyclobutyl-5-methyl-hexanoic acid;
3-Amino-7-cyclopropyl-5-methyl-heptanoic acid;
3-Amino-7-cyclobutyl-5-methyl-heptanoic acid;
3-Amino-7-cyclopentyl-5-methyl-heptanoic acid;
3-Amino-7-cyclohexyl-5-methyl-heptanoic acid;
3-Amino-8-cyclopropyl-5-methyl-octanoic acid;
3-Amino-8-cyclobutyl-5-methyl-octanoic acid;
3-Amino-8-cyclopentyl-5-methyl-octanoic acid;
3-Amino-8-cyclohexyl-5-methyl-octanoic acid;
3-Amino-6-cyclopropyl-5,5-dimethyl-hexanoic acid;
3-Amino-6-cyclobutyl-5,5-dimethyl-hexanoic acid;
3-Amino-6-cyclopentyl-5,5-dimethyl-hexanoic acid;
3-Amino-6-cyclohexyl-5,5-dimethyl-hexanoic acid;
3-Amino-7-cyclopropyl-5,5-dimethyl-heptanoic acid;
3-Amino-7-cyclobutyl-5,5-dimethyl-heptanoic acid;
3-Amino-7-cyclopentyl-5,5-dimethyl-heptanoic acid;
3-Amino-7-cyclohexyl-5,5-dimethyl-heptanoic acid;
(3S,5R)-3-Amino-6-cyclobutyl-5-methyl-hexanoic acid;
(3S,5R)-3-Amino-7-cyclopropyl-5-methyl-heptanoic acid;
(3S,5R)-3-Amino-7-cyclobutyl-5-methyl-heptanoic acid;
(3S,5R)-3-Amino-7-cyclopentyl-5-methyl-heptanoic acid;
(3S,5R)-3-Amino-7-cyclohexyl-5-methyl-heptanoic acid;
(3S,5R)-3-Amino-8-cyclopropyl-5-methyl-octanoic acid;
(3S,5R)-3-Amino-8-cyclobutyl-5-methyl-octanoic acid;
(3S,5R)-3-Amino-8-cyclopentyl-5-methyl-octanoic acid;
(3S,5R)-3-Amino-8-cyclohexyl-5-methyl-octanoic acid;
(3S,5S)-3-Amino-6-cyclobutyl-5-methyl-hexanoic acid;
(3S,5S)-3-Amino-7-cyclopropyl-5-methyl-heptanoic acid;
(3S,5S)-3-Amino-7-cyclobutyl-5-methyl-heptanoic acid;
(3S,5S)-3-Amino-7-cyclopentyl-5-methyl-heptanoic acid;
(3S,5S)-3-Amino-7-cyclohexyl-5-methyl-heptanoic acid;
(3S,5S)-3-Amino-8-cyclopropyl-5-methyl-octanoic acid;
(3S,5S)-3-Amino-8-cyclobutyl-5-methyl-octanoic acid;
(3S,5S)-3-Amino-8-cyclopentyl-5-methyl-octanoic acid;
(3S,5S)-3-Amino-8-cyclohexyl-5-methyl-octanoic acid;
(3S)-3-Amino-6-cyclopropyl-5,5-dimethyl-hexanoic acid;
(3S)-3-Amino-6-cyclobutyl-5,5-dimethyl-hexanoic acid;
(3S)-3-Amino-6-cyclopentyl-5,5-dimethyl-hexanoic acid;
(3S)-3-Amino-6-cyclohexyl-5,5-dimethyl-hexanoic acid;
(3S)-3-Amino-7-cyclopropyl-5,5-dimethyl-heptanoic acid;
(3S)-3-Amino-7-cyclobutyl-5,5-dimethyl-heptanoic acid;
(3S)-3-Amino-7-cyclopentyl-5,5-dimethyl-heptanoic acid; and
(3S)-3-Amino-7-cyclohexyl-5,5-dimethyl-heptanoic acid;

Other specific embodiments of this invention include the following compounds of the formula I and their pharmaceutically acceptable salts:

3-Amino-5-methyl-heptanoic acid;
3-Amino-5-methyl-octanoic acid;
3-Amino-5-methyl-nonanoic acid;
3-Amino-5,5-dimethyl-nonanoic acid;
3-Amino-5,5-dimethyl-decanoic acid;
(3S)-3-Amino-5,5-dimethyl-nonanoic acid; and
(3S)-3-Amino-5,5-dimethyl-decanoic acid.

This invention also relates to compounds of the formula IA:

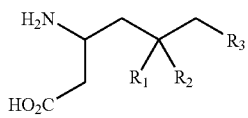

wherein
R₁ is hydrogen or (C₁–C₃)alkyl optionally substituted with from one to five fluorine atoms;
R₂ is hydrogen or (C₁–C₃)alkyl optionally substituted with from one to five fluorine atoms; or
R₁ and R₂, together with the carbon to which they are attached, form a three to six membered cycloalkyl ring;
R₃ is (C₁–C₆)alkyl, (C₃–C₆)cycloalkyl, (C₃–C₆)cycloalkyl-(C₁–C₃)alkyl, phenyl, phenyl-(C₁–C₃)alkyl, pyridyl, pyridyl-(C₁–C₃)alkyl, phenyl-N(H)—, or pyridyl-N(H)—, wherein each of the foregoing alkyl moieties can be optionally substituted with from one to five fluorine atoms, preferably with from zero to three fluorine atoms, and wherein said phenyl and said pyridyl and the phenyl and pyridyl moieties of said phenyl-(C₁–C₃)alkyl and said pyridyl-(C₁–C₃)alkyl, respectively, can be optionally substituted with from one to three substituents, preferably with from zero to two substituents, independently selected from chloro, fluoro, amino, nitro, cyano, (C₁–C₃)alkylamino, (C₁–C₃)alkyl optionally substituted with from one to three fluorine atoms and (C₁–C₃)alkoxy optionally substituted with from one to three fluorine atoms;
with the proviso that when R₁ is hydrogen, R₂ is not hydrogen; and the pharmaceutically acceptable salts of such compounds.

This invention also relates to compounds of the formula IA-1

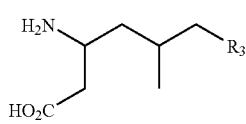

wherein R₃ is defined as for formula I above, and the pharmaceutically acceptable salts of such compounds.

Other specific embodiments of this invention include the following compounds of the formula IA and their pharmaceutically acceptable salts:
3-Amino-5-methyl-8-phenylamino-octanoic acid;
3-Amino-5-methyl-7-phenylamino-heptanoic acid;
3-Amino-5-methyl-6-phenylamino-hexanoic acid;
(3S,5R)-3-Amino-5-methyl-8-phenylamino-octanoic acid;
(3S,5R)-3-Amino-5-methyl-7-phenylamino-heptanoic acid;
(3S,5R)-3-Amino-5-methyl-6-phenylamino-hexanoic acid;
(3S,5S)-3-Amino-5-methyl-8-phenylamino-octanoic acid;
(3S,5S)-3-Amino-5-methyl-7-phenylamino-heptanoic acid;
(3S,5S)-3-Amino-5-methyl-6-phenylamino-hexanoic acid;
3-Amino-5-methyl-8-phenyl-octanoic acid;
3-Amino-8-(2-fluoro-phenyl)-5-methyl-octanoic acid;
3-Amino-8-(3-fluoro-phenyl)-5-methyl-octanoic acid;
3-Amino-8-(4-fluoro-phenyl)-5-methyl-octanoic acid;
3-Amino-8-(2-trifluoro-phenyl)-5-methyl-octanoic acid;
3-Amino-8-(3-trifluoro-phenyl)-5-methyl-octanoic acid;
3-Amino-8-(4-trifluoro-phenyl)-5-methyl-octanoic acid;
3-Amino-5-methyl-8-o-tolyl-octanoic acid;
3-Amino-5-methyl-8-m-tolyl-octanoic acid;
3-Amino-5-methyl-8-p-tolyl-octanoic acid;
3-Amino-5-methyl-8-p-tolyl-octanoic acid;
3-Amino-8-(2,3-difluoro-phenyl)-5-methyl-octanoic acid;
3-Amino-8-(2,4-difluoro-phenyl)-5-methyl-octanoic acid;
3-Amino-8-(2,5-difluoro-phenyl)-5-methyl-octanoic acid;
3-Amino-8-(2,6-difluoro-phenyl)-5-methyl-octanoic acid;
(3S,5R)-3-Amino-5-methyl-8-phenyl-octanoic acid;
(3S,5S)-3-Amino-5-methyl-8-phenyl-octanoic acid;
(3S,5R)-3-Amino-8-(2-fluoro-phenyl)-5-methyl-octanoic acid;
(3S,5S)-3-Amino-8-(2-fluoro-phenyl)-5-methyl-octanoic acid;
(3S,5R)-3-Amino-8-(3-fluoro-phenyl)-5-methyl-octanoic acid;
(3S,5S)-3-Amino-8-(3-fluoro-phenyl)-5-methyl-octanoic acid;
(3S,5R)-3-Amino-8-(4-fluoro-phenyl)-5-methyl-octanoic acid;
(3S,5S)-3-Amino-8-(4-fluoro-phenyl)-5-methyl-octanoic acid;
(3S,5R)-3-Amino-8-(2-trifluoro-phenyl)-5-methyl-octanoic acid;
(3S,5S)-3-Amino-8-(2-trifluoro-phenyl)-5-methyl-octanoic acid;
(3S,5R)-3-Amino-8-(3-trifluoro-phenyl)-5-methyl-octanoic acid;
(3S,5S)-3-Amino-8-(3-trifluoro-phenyl)-5-methyl-octanoic acid;
(3S,5R)-3-Amino-8-(4-trifluoro-phenyl)-5-methyl-octanoic acid;
(3S,5S)-3-Amino-8-(4-trifluoro-phenyl)-5-methyl-octanoic acid;
(3S,5R)-3-Amino-5-methyl-8-o-tolyl-octanoic acid;
(3S,5S)-3-Amino-5-methyl-8-o-tolyl-octanoic acid;
(3S,5R)-3-Amino-5-methyl-8-m-tolyl-octanoic acid;
(3S,5S)-3-Amino-5-methyl-8-m-tolyl-octanoic acid;
(3S,5R)-3-Amino-5-methyl-8-p-tolyl-octanoic acid
(3S,5S)-3-Amino-5-methyl-8-p-tolyl-octanoic acid;
(3S,5R)-3-Amino-8-(2,3-difluoro-phenyl)5-methyl-octanoic acid;
(3S,5S)-3-Amino-8-(2,3-difluoro-phenyl)5-methyl-octanoic acid;
(3S,5R)-3-Amino-8-(2,4-difluoro-phenyl)5-methyl-octanoic acid;
(3S,5S)-3-Amino-8-(2,4-difluoro-phenyl)5-methyl-octanoic acid;
(3S,5R)-3-Amino-8-(2,5-difluoro-phenyl)5-methyl-octanoic acid;
(3S,5S)-3-Amino-8-(2,5-difluoro-phenyl)5-methyl-octanoic acid;
(3S,5R)-3-Amino-8-(2,6-difluoro-phenyl)-5-methyl-octanoic acid; and
(3S,5S)-3-Amino-8-(2,6-difluoro-phenyl)-5-methyl-octanoic acid.

Preferred compounds of this invention include those of the formula IA-2,

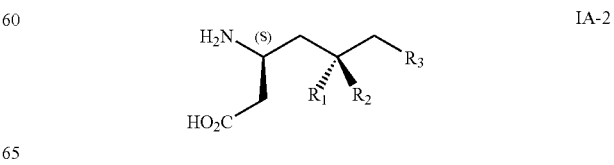

wherein R₁, R₂, and R₃ are defined as for formula I above.

Examples of more preferred compounds of this invention are compounds of the formula IA-2 wherein $R_1$ is hydrogen, $R_2$ is methyl and $R_3$ is defined as for formula I above.

Examples of specific embodiments of this invention are the following compounds of the formula IA-2 and their pharmaceutically acceptable salts:
(3S,5R)-3-Amino-5-methyl-heptanoic acid;
(3S,5R)-3-Amino-5-methyl-octanoic acid; and
(3S,5R)-3-Amino-5-methyl-nonanoic acid.

This invention also relates to compounds of the formula IB

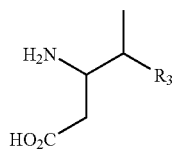

and their pharmaceutically acceptable salts wherein $R_3$ is defined as above and wherein said compounds are selected from the following compounds and their pharmaceutically acceptable salts:
3-Amino-4,5-dimethyl-hexanoic acid;
3-Amino-4,6-dimethyl-heptanoic acid;
3-Amino-4,7-dimethyl-octanoic acid;
3-Amino-4,8-dimethyl-nonanoic acid;
3-Amino-4,9-dimethyl-decanoic acid;
3-Amino-4-cyclopropyl-pentanoic acid;
3-Amino-4-cyclobutyl-pentanoic acid;
3-Amino-4-cyclopentyl-pentanoic acid;
3-Amino-4-cyclohexyl-pentanoic acid;
3-Amino-5-cyclopropyl-4-methyl-pentanoic acid;
3-Amino-5-cyclobutyl-4-methyl-pentanoic acid;
3-Amino-5-cyclopentyl-4-methyl-pentanoic acid;
3-Amino-5-cyclohexyl-4-methyl-pentanoic acid;
3-Amino-6-cyclopropyl-4-methyl-hexanoic acid;
3-Amino-6-cyclobutyl-4-methyl-hexanoic acid;
3-Amino-6-cyclopentyl-4-methyl-hexanoic acid;
3-Amino-6-cyclohexyl-4-methyl-hexanoic acid;
3-Amino-7-cyclopropyl-4-methyl-heptanoic acid;
3-Amino-7-cyclobutyl-4-methyl-heptanoic acid;
3-Amino-7-cyclopentyl-4-methyl-heptanoic acid;
3-Amino-7-cyclohexyl-4-methyl-heptanoic acid;
3-Amino-8-cyclopropyl-4-methyl-octanoic acid;
3-Amino-8-cyclobutyl-4-methyl-octanoic acid;
3-Amino-8-cyclopentyl-4-methyl-octanoic acid;
3-Amino-8-cyclohexyl-4-methyl-octanoic acid;
3-Amino-9-cyclopropyl-4-methyl-nonanoic acid;
3-Amino-9-cyclobutyl-4-methyl-nonanoic acid;
3-Amino-9-cyclopentyl-4-methyl-nonanoic acid;
3-Amino-9-cyclohexyl-4-methyl-nonanoic acid;
3-Amino-4-methyl-octanoic acid;
3-Amino-4-methyl-nonanoic acid;
3-Amino-4-methyl-decanoic acid;
(3R,4R)-3-Amino-4,5-dimethyl-hexanoic acid;
(3R,4R)-3-Amino-4,6-dimethyl-heptanoic acid;
(3R,4R)-3-Amino-4,7-dimethyl-octanoic acid;
(3R,4R)-3-Amino-4,8-dimethyl-nonanoic acid;
(3R,4R)-3-Amino-4,9-dimethyl-decanoic acid;
(3R,4R)-3-Amino-4-cyclopropyl-pentanoic acid;
(3R,4R)-3-Amino-4-cyclobutyl-pentanoic acid;
(3R,4R)-3-Amino-4-cyclopentyl-pentanoic acid;
(3R,4R)-3-Amino-4-cyclohexyl-pentanoic acid;
(3R,4R)-3-Amino-5-cyclopropyl-4-methyl-pentanoic acid;
(3R,4R)-3-Amino-5-cyclobutyl-4-methyl-pentanoic acid;
(3R,4R)-3-Amino-5-cyclopentyl-4-methyl-pentanoic acid;
(3R,4R)-3-Amino-5-cyclohexyl-4-methyl-pentanoic acid;
(3R,4R)-3-Amino-6-cyclopropyl-4-methyl-hexanoic acid;
(3R,4R)-3-Amino-6-cyclobutyl-4-methyl-hexanoic acid;
(3R,4R)-3-Amino-6-cyclopentyl-4-methyl-hexanoic acid;
(3R,4R)-3-Amino-6-cyclohexyl-4-methyl-hexanoic acid;
(3R,4R)-3-Amino-7-cyclopropyl-4-methyl-heptanoic acid;
(3R,4R)-3-Amino-7-cyclobutyl-4-methyl-heptanoic acid;
(3R,4R)-3-Amino-7-cyclopentyl-4-methyl-heptanoic acid;
(3R,4R)-3-Amino-7-cyclohexyl-4-methyl-heptanoic acid;
(3R,4R)-3-Amino-8-cyclopropyl-4-methyl-octanoic acid;
(3R,4R)-3-Amino-8-cyclobutyl-4-methyl-octanoic acid;
(3R,4R)-3-Amino-8-cyclopentyl-4-methyl-octanoic acid;
(3R,4R)-3-Amino-8-cyclohexyl-4-methyl-octanoic acid;
(3R,4R)-3-Amino-9-cyclopropyl-4-methyl-nonanoic acid;
(3R,4R)-3-Amino-9-cyclobutyl-4-methyl-nonanoic acid;
(3R,4R)-3-Amino-9-cyclopentyl-4-methyl-nonanoic acid;
(3R,4R)-3-Amino-9-cyclohexyl-4-methyl-nonanoic acid;
(3R,4R)-3-Amino-4-methyl-octanoic acid;
(3R,4R)-3-Amino-4-methyl-nonanoic acid;
(3R,4R)-3-Amino-4-methyl-decanoic acid;
(3R,4S)-3-Amino-4,5-dimethyl-hexanoic acid;
(3R,4S)-3-Amino-4,6-dimethyl-heptanoic acid;
(3R,4S)-3-Amino-4,7-dimethyl-octanoic acid;
(3R,4S)-3-Amino-4,8-dimethyl-nonanoic acid;
(3R,4S)-3-Amino-4,9-dimethyl-decanoic acid;
(3R,4S)-3-Amino-4-cyclopropyl-pentanoic acid;
(3R,4S)-3-Amino-4-cyclobutyl-pentanoic acid;
(3R,4S)-3-Amino-4-cyclopentyl-pentanoic acid;
(3R,4S)-3-Amino-4-cyclohexyl-pentanoic acid;
(3R,4S)-3-Amino-5-cyclopropyl-4-methyl-pentanoic acid;
(3R,4S)-3-Amino-5-cyclobutyl-4-methyl-pentanoic acid;
(3R,4S)-3-Amino-5-cyclopentyl-4-methyl-pentanoic acid;
(3R,4S)-3-Amino-5-cyclohexyl-4-methyl-pentanoic acid;
(3R,4S)-3-Amino-6-cyclopropyl-4-methyl-hexanoic acid;
(3R,4S)-3-Amino-6-cyclobutyl-4-methyl-hexanoic acid;
(3R,4S)-3-Amino-6-cyclopentyl-4-methyl-hexanoic acid;
(3R,4S)-3-Amino-6-cyclohexyl-4-methyl-hexanoic acid;
(3R,4S)-3-Amino-7-cyclopropyl-4-methyl-heptanoic acid;
(3R,4S)-3-Amino-7-cyclobutyl-4-methyl-heptanoic acid;
(3R,4S)-3-Amino-7-cyclopentyl-4-methyl-heptanoic acid;
(3R,4S)-3-Amino-7-cyclohexyl-4-methyl-heptanoic acid;
(3R,4S)-3-Amino-8-cyclopropyl-4-methyl-octanoic acid;
(3R,4S)-3-Amino-8-cyclobutyl-4-methyl-octanoic acid;
(3R,4S)-3-Amino-8-cyclopentyl-4-methyl-octanoic acid;
(3R,4S)-3-Amino-8-cyclohexyl-4-methyl-octanoic acid;
(3R,4S)-3-Amino-9-cyclopropyl-4-methyl-nonanoic acid;
(3R,4S)-3-Amino-9-cyclobutyl-4-methyl-nonanoic acid;
(3R,4S)-3-Amino-9-cyclopentyl-4-methyl-nonanoic acid;
(3R,4S)-3-Amino-9-cyclohexyl-4-methyl-nonanoic acid;
(3R,4S)-3-Amino-4-methyl-octanoic acid;
(3R,4S)-3-Amino-4-methyl-nonanoic acid; and
(3R,4S)-3-Amino-4-methyl-decanoic acid.

This invention also relates to the compounds of the formula IC

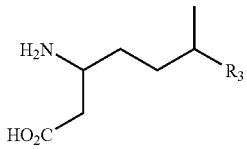

and their pharmaceutically acceptable salts wherein $R_3$ is defined as above and wherein said compounds are selected from the following compounds and their pharmaceutically acceptable salts:
3-Amino-6-methyl-decanoic acid;
3-Amino-6-cyclopropyl-heptanoic acid;
3-Amino-6-cyclobutyl-heptanoic acid;
3-Amino-6-cyclopentyl-heptanoic acid;
3-Amino-6-cyclohexyl-heptanoic acid;
3-Amino-7-cyclopropyl-6-methyl-heptanoic acid;
3-Amino-7-cyclobutyl-6-methyl-heptanoic acid;
3-Amino-7-cyclopentyl-6-methyl-heptanoic acid;
3-Amino-7-cyclohexyl-6-methyl-heptanoic acid;
3-Amino-8-cyclopropyl-6-methyl-octanoic acid;
3-Amino-8-cyclobutyl-6-methyl-octanoic acid;
3-Amino-8-cyclopentyl-6-methyl-octanoic acid;
3-Amino-8-cyclohexyl-6-methyl-octanoic acid;
3-Amino-9-cyclopropyl-6-methyl-nonanoic acid;
3-Amino-9-cyclobutyl-6-methyl-nonanoic acid;
3-Amino-9-cyclopentyl-6-methyl-nonanoic acid;
3-Amino-9-cyclohexyl-6-methyl-nonanoic acid;
3-Amino-10-cyclopropyl-6-methyl-decanoic acid;
3-Amino-10-cyclobutyl-6-methyl-decanoic acid;
3-Amino-10-cyclopentyl-6-methyl-decanoic acid;
3-Amino-10-cyclohexyl-6-methyl-decanoic acid;
3-Amino-6-isopropyl-heptanoic acid;
3-Amino-6,8-dimethyl-nonanoic acid;
3-Amino-6,9-dimethyl-decanoic acid;
(3S,6R)-3-Amino-6-methyl-decanoic acid;
(3S,6R)-3-Amino-6-cyclopropyl-heptanoic acid;
(3S,6R)-3-Amino-6-cyclobutyl-heptanoic acid;
(3S,6R)-3-Amino-6-cyclopentyl-heptanoic acid;
(3S,6R)-3-Amino-6-cyclohexyl-heptanoic acid;
(3S,6R)-3-Amino-7-cyclopropyl-6-methyl-heptanoic acid;
(3S,6R)-3-Amino-7-cyclobutyl-6-methyl-heptanoic acid;
(3S,6R)-3-Amino-7-cyclopentyl-6-methyl-heptanoic acid;
(3S,6R)-3-Amino-7-cyclohexyl-6-methyl-heptanoic acid;
(3S,6R)-3-Amino-8-cyclopropyl-6-methyl-octanoic acid;
(3S,6R)-3-Amino-8-cyclobutyl-6-methyl-octanoic acid;
(3S,6R)-3-Amino-8-cyclopentyl-6-methyl-octanoic acid;
(3S,6R)-3-Amino-8-cyclohexyl-6-methyl-octanoic acid;
(3S,6R)-3-Amino-9-cyclopropyl-6-methyl-nonanoic acid;
(3S,6R)-3-Amino-9-cyclobutyl-6-methyl-nonanoic acid;
(3S,6R)-3-Amino-9-cyclopentyl-6-methyl-nonanoic acid;
(3S,6R)-3-Amino-9-cyclohexyl-6-methyl-nonanoic acid;
(3S,6R)-3-Amino-10-cyclopropyl-6-methyl-decanoic acid;
(3S,6R)-3-Amino-10-cyclobutyl-6-methyl-decanoic acid;
(3S,6R)-3-Amino-10-cyclopentyl-6-methyl-decanoic acid;
(3S,6R)-3-Amino-10-cyclohexyl-6-methyl-decanoic acid;
(3S,6R)-3-Amino-6-isopropyl-heptanoic acid;
(3S,6R)-3-Amino-6,8-dimethyl-nonanoic acid;
(3S,6R)-3-Amino-6,9-dimethyl-decanoic acid;
(3S,6S)-3-Amino-6-methyl-octanoic acid;
(3S,6S)-3-Amino-6-methyl-nonanoic acid;
(3S,6S)-3-Amino-6-methyl-decanoic acid;
(3S,6S)-3-Amino-6-cyclopropyl-heptanoic acid;
(3S,6S)-3-Amino-6-cyclobutyl-heptanoic acid;
(3S,6S)-3-Amino-6-cyclopentyl-heptanoic acid;
(3S,6S)-3-Amino-6-cyclohexyl-heptanoic acid;
(3S,6S)-3-Amino-7-cyclopropyl-6-methyl-heptanoic acid;
(3S,6S)-3-Amino-7-cyclobutyl-6-methyl-heptanoic acid;
(3S,6S)-3-Amino-7-cyclopentyl-6-methyl-heptanoic acid;
(3S,6S)-3-Amino-7-cyclohexyl-6-methyl-heptanoic acid;
(3S,6S)-3-Amino-8-cyclopropyl-6-methyl-octanoic acid;
(3S,6S)-3-Amino-8-cyclobutyl-6-methyl-octanoic acid;
(3S,6S)-3-Amino-8-cyclopentyl-6-methyl-octanoic acid;
(3S,6S)-3-Amino-8-cyclohexyl-6-methyl-octanoic acid;
(3S,6S)-3-Amino-9-cyclopropyl-6-methyl-nonanoic acid;
(3S,6S)-3-Amino-9-cyclobutyl-6-methyl-nonanoic acid;
(3S,6S)-3-Amino-9-cyclopentyl-6-methyl-nonanoic acid;
(3S,6S)-3-Amino-9-cyclohexyl-6-methyl-nonanoic acid;
(3S,6S)-3-Amino-10-cyclopropyl-6-methyl-decanoic acid;
(3S,6S)-3-Amino-10-cyclobutyl-6-methyl-decanoic acid;
(3S,6S)-3-Amino-10-cyclopentyl-6-methyl-decanoic acid;
(3S,6S)-3-Amino-10-cyclohexyl-6-methyl-decanoic acid;
(3S,6S)-3-Amino-6-isopropyl-heptanoic acid;
(3S,6S)-3-Amino-6,8-dimethyl-nonanoic acid; and
(3S,6S)-3-Amino-6,9-dimethyl-decanoic acid.

This invention also relates to compounds of the formula II:

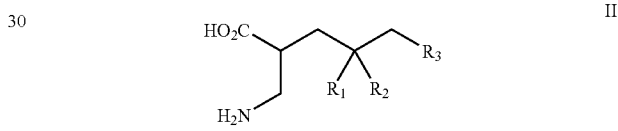

wherein $R_1$, $R_2$, and $R_3$ are defined as for formula I above, and the pharmaceutically acceptable salts of such compounds.

Examples of specific embodiments of this invention are the following compound of formula IV and its pharmaceutically acceptable salts: 2-aminomethyl-4-propyl-heptanoic acid.

This invention also relates to compounds of the formula IIA

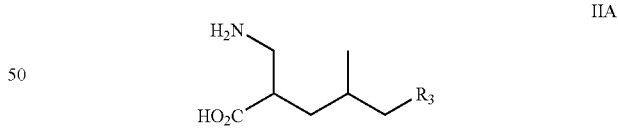

wherein $R_3$ is defined as for formula I above, and the pharmaceutically acceptable salts of such compounds.

Other specific embodiments of this invention include the following compounds of the formula II and their pharmaceutically acceptable salts:
2-Aminomethyl-4-methyl-7-phenyl-heptanoic acid;
2-Aminomethyl-4-methyl-6-phenyl-hexanoic acid;
2-Aminomethyl-7-(4-fluoro-phenyl)-4-methyl-heptanoic acid;
2-Aminomethyl-7-(3-fluoro-phenyl)-4-methyl-heptanoic acid;
2-Aminomethyl-7-(2-fluoro-phenyl)-4-methyl-heptanoic acid;

2-Aminomethyl-7-(2,4-difluoro-phenyl)-4-methyl-heptanoic acid;
2-Aminomethyl-7-(3,4-difluoro-phenyl)-4-methyl-heptanoic acid;
2-Aminomethyl-4-methyl-7-(2-trifluoromethyl-phenyl)-heptanoic acid;
2-Aminomethyl-4-methyl-7-(3-trifluoromethyl-phenyl)-heptanoic acid;
2-Aminomethyl-4-methyl-7-(4-trifluoromethyl-phenyl)-heptanoic acid;
2-Aminomethyl-4-methyl-6-phenylamino-hexanoic acid;
2-Aminomethyl-4-methyl-7-phenylamino-heptanoic acid;
2-Aminomethyl-4-methyl-8-phenylamino-octancoic acid;
(2R,4R)-2-Aminomethyl-4-methyl-7-phenyl-heptanoic acid;
(2R,4R)-2-Aminomethyl-4-methyl-6-phenyl-hexanoic acid;
(2R,4R)-2-Aminomethyl-7-(4-fluoro-phenyl)-4-methyl-heptanoic acid;
(2R,4R)-2-Aminomethyl-7-(3-fluoro-phenyl)-4-methyl-heptanoic acid;
(2R,4R)-2-Aminomethyl-7-(2-fluoro-phenyl)-4-methyl-heptanoic acid;
(2R,4R)-2-Aminomethyl-7-(2,4-difluoro-phenyl)-4-methyl-heptanoic acid;
(2R,4R)-2-Aminomethyl-7-(3,4-difluoro-phenyl)-4-methyl-heptanoic acid;
(2R,4R)-2-Aminomethyl-4-methyl-7-(2-trifluoromethyl-phenyl)-heptanoic acid;
(2R,4R)-2-Aminomethyl-4-methyl-7-(3-trifluoromethyl-phenyl)-heptanoic acid;
(2R,4R)-2-Aminomethyl-4-methyl-7-(4-trifluoromethyl-phenyl)-heptanoic acid;
(2R,4R)-2-Aminomethyl-4-methyl-6-phenylamino-hexanoic acid;
(2R,4R)-2-Aminomethyl-4-methyl-7-phenylamino-heptanoic acid;
(2R,4R)-2-Aminomethyl-4-methyl-8-phenylamino-octancoic acid;
(2R,4S)-2-Aminomethyl-4-methyl-7-phenyl-heptanoic acid;
(2R,4S)-2-Aminomethyl-4-methyl-6-phenyl-hexanoic acid;
(2R,4S)-2-Aminomethyl-7-(4-fluoro-phenyl)-4-methyl-heptanoic acid;
(2R,4S)-2-Aminomethyl-7-(3-fluoro-phenyl)-4-methyl-heptanoic acid;
(2R,4S)-2-Aminomethyl-7-(2-fluoro-phenyl)-4-methyl-heptanoic acid;
(2R,4S)-2-Aminomethyl-7-(2,4-difluoro-phenyl)-4-methyl-heptanoic acid;
(2R,4S)-2-Aminomethyl-7-(3,4-difluoro-phenyl)-4-methyl-heptanoic acid;
(2R,4S)-2-Aminomethyl-4-methyl-7-(2-trifluoromethyl-phenyl)-heptanoic acid;
(2R,4S)-2-Aminomethyl-4-methyl-7-(3-trifluoromethyl-phenyl)-heptanoic acid;
(2R,4S)-2-Aminomethyl-4-methyl-7-(4-trifluoromethyl-phenyl)-heptanoic acid;
(2R,4S)-2-Aminomethyl-4-methyl-6-phenylamino-hexanoic acid;
(2R,4S)-2-Aminomethyl-4-methyl-7-phenylamino-heptanoic acid;
(2R,4S)-2-Aminomethyl-4-methyl-8-phenylamino-octanoic acid;
(2R,4S)-2-Aminomethyl-6-cyclohexyl-4-ethyl-hexanoic acid;
2-Aminomethyl-3-(1-methyl-cyclopropyl)-propionic acid
2-Aminomethyl-3-(1-ethyl-cyclopropyl)-propionic acid
2-Aminomethyl-3-(1-propyl-cyclopropyl)-propionic acid
2-Aminomethyl-3-(1-isopropyl-cyclopropyl)-propionic acid
2-Aminomethyl-3-(1-butyl-cyclopropyl)-propionic acid
2-Aminomethyl-3-(1-isobutyl-cyclopropyl)-propionic acid
2-Aminomethyl-3-[1-(4-methyl-pentyl)-cyclopropyl]-propionic acid
2-Aminomethyl-3-(1-methyl-cyclobutyl)-propionic acid
2-Aminomethyl-3-(1-ethyl-cyclobutyl)-propionic acid
2-Aminomethyl-3-(1-propyl-cyclobutyl)-propionic acid
2-Aminomethyl-3-(1-methyl-cyclopentyl)-propionic acid
2-Aminomethyl-3-(1-ethyl-cyclopentyl)-propionic acid
2-Aminomethyl-3-(1-propyl-cyclopentyl)-propionic acid
2-Aminomethyl-3-(1-methyl-cyclohexyl)-propionic acid
2-Aminomethyl-3-(1-ethyl-cyclohexyl)-propionic acid
2-Aminomethyl-3-(1-propyl-cyclohexyl)-propionic acid
2-Aminomethyl-4-ethyl-hexanoic acid
2-Aminomethyl-4-ethyl-5-methyl-hexanoic acid
2-Aminomethyl-4-ethyl-heptanoic acid
2-Aminomethyl-4-ethyl-6-methyl-heptanoic acid
2-Aminomethyl-4-ethyl-octanoic acid
2-Aminomethyl-4-ethyl-7-methyl-octanoic acid
2-Aminomethyl-4-ethyl-nonanoic acid
2-Aminomethyl-4-ethyl-8-methyl-nonanoic acid
2-Aminomethyl-4,4-dimethyl-heptanoic acid
2-Aminomethyl-4,4,8-trimethyl-nonanoic acid
2-Aminomethyl-5-ethyl-heptanoic acid
2-Aminomethyl-5-ethyl-6-methyl-heptanoic acid
2-Aminomethyl-7-cyclopropyl-5-ethyl-heptanoic acid
2-Aminomethyl-7-cyclobutyl-5-ethyl-heptanoic acid
2-Aminomethyl-7-cyclopentyl-5-ethyl-heptanoic acid
2-Aminomethyl-7-cyclohexyl-5-ethyl-heptanoic acid
2-Aminomethyl-5-ethyl-octanoic acid
2-Aminomethyl-5-ethyl-7-methyl-octanoic acid
2-Aminomethyl-5-ethyl-nonanoic acid
2-Aminomethyl-5-ethyl-8-methyl-nonanoic acid
2-Aminomethyl-4-cyclopropyl-butyric acid
2-Aminomethyl-4-(1-methyl-cyclopropyl)-butyric acid
2-Aminomethyl-4-(1-ethyl-cyclopropyl)-butyric acid
2-Aminomethyl-4-cyclobutyl-butyric acid
2-Aminomethyl-4-(1-methyl-cyclobutyl)-butyric acid
2-Aminomethyl-4-(1-ethyl-cyclobutyl)-butyric acid
2-Aminomethyl-4-cyclopentyl-butyric acid
2-Aminomethyl-4-(1-methyl-cyclopentyl)-butyric acid
2-Aminomethyl-4-(1-ethyl-cyclopentyl)-butyric acid
2-Aminomethyl-4-cyclohexyl-butyric acid
2-Aminomethyl-4-(1-methyl-cyclohexyl)-butyric acid
2-Aminomethyl-4-(1-ethyl-cyclohexyl)-butyric acid
(2R,4S)-2-Aminomethyl-6-cyclopentyl-4-ethyl-hexanoic acid;
(2R,4S)-2-Aminomethyl-6-cyclobutyl-4-ethyl-hexanoic acid; and
(2R,4S)-2-Aminomethyl-6-cyclopropyl-4-ethyl-hexanoic acid.

Other specific embodiments of this invention include the following compounds of the formula IIA and their pharmaceutically acceptable salts:
2-Aminomethyl-4-methyl-hexanoic acid;
2-Aminomethyl-4-methyl-heptanoic acid;
2-Aminomethyl-4-methyl-octanoic acid;
2-Aminomethyl-4-methyl-nonanoic acid;
2-Aminomethyl-4-methyl-decanoic acid;
(2R,4R)-2-Aminomethyl-4-methyl-hexanoic acid;
(2R,4R)-2-Aminomethyl-4-methyl-heptanoic acid;
(2R,4R)-2-Aminomethyl-4-methyl-octanoic acid;
(2R,4R)-2-Aminomethyl-4-methyl-nonanoic acid;
(2R,4R)-2-Aminomethyl-4-methyl-decanoic acid;
(2R,4S)-2-Aminomethyl-4-methyl-hexanoic acid;

(2R,4S)-2-Aminomethyl-4-methyl-heptanoic acid;
(2R,4S)-2-Aminomethyl-4-methyl-octanoic acid;
(2R,4S)-2-Aminomethyl-4-methyl-nonanoic acid;
(2R,4S)-2-Aminomethyl-4-methyl-decanoic acid;
2-Aminomethyl-5-cyclopropyl-4-methyl-pentanoic acid;
2-Aminomethyl-5-cyclobutyl-4-methyl-pentanoic acid;
2-Aminomethyl-5-cyclopentyl-4-methyl-pentanoic acid;
2-Aminomethyl-5-cyclohexyl-4-methyl-pentanoic acid;
2-Aminomethyl-6-cyclopropyl-4-methyl-hexanoic acid;
2-Aminomethyl-6-cyclobutyl-4-methyl-hexanoic acid;
2-Aminomethyl-6-cyclopentyl-4-methyl-hexanoic acid;
2-Aminomethyl-6-cyclohexyl-4-methyl-hexanoic acid;
2-Aminomethyl-7-cyclopropyl-4-methyl-heptanoic acid;
2-Aminomethyl-7-cyclobutyl-4-methyl-heptanoic acid;
2-Aminomethyl-7-cyclopentyl-4-methyl-heptanoic acid;
2-Aminomethyl-7-cyclohexyl-4-methyl-heptanoic acid;
2-Aminomethyl-8-cyclopropyl-4-methyl-octanoic acid;
2-Aminomethyl-8-cyclobutyl-4-methyl-octanoic acid;
2-Aminomethyl-8-cyclopentyl-4-methyl-octanoic acid;
2-Aminomethyl-8-cyclohexyl-4-methyl-octanoic acid;
(2R,4S)-2-Aminomethyl-5-cyclopropyl-4-methyl-pentanoic acid;
(2R,4S)-2-Aminomethyl-5-cyclobutyl-4-methyl-pentanoic acid;
(2R,4S)-2-Aminomethyl-5-cyclopentyl-4-methyl-pentanoic acid;
(2R,4S)-2-Aminomethyl-5-cyclohexyl-4-methyl-pentanoic acid;
(2R,4S)-2-Aminomethyl-6-cyclopropyl-4-methyl-hexanoic acid;
(2R,4S)-2-Aminomethyl-6-cyclobutyl-4-methyl-hexanoic acid;
(2R,4S)-2-Aminomethyl-6-cyclopentyl-4-methyl-hexanoic acid;
(2R,4S)-2-Aminomethyl-6-cyclohexyl-4-methyl-hexanoic acid;
(2R,4S)-2-Aminomethyl-7-cyclopropyl-4-methyl-heptanoic acid;
(2R,4S)-2-Aminomethyl-7-cyclobutyl-4-methyl-heptanoic acid;
(2R,4S)-2-Aminomethyl-7-cyclopentyl-4-methyl-heptanoic acid;
(2R,4S)-2-Aminomethyl-7-cyclohexyl-4-methyl-heptanoic acid;
(2R,4S)-2-Aminomethyl-8-cyclopropyl-4-methyl-octanoic acid;
(2R,4S)-2-Aminomethyl-8-cyclobutyl-4-methyl-octanoic acid;
(2R,4S)-2-Aminomethyl-8-cyclopentyl-4-methyl-octanoic acid;
(2R,4S)-2-Aminomethyl-8-cyclohexyl-4-methyl-octanoic acid;
(2R,4R)-2-Aminomethyl-5-cyclopropyl-4-methyl-pentanoic acid;
(2R,4R)-2-Aminomethyl-5-cyclobutyl-4-methyl-pentanoic acid;
(2R,4R)-2-Aminomethyl-5-cyclopentyl-4-methyl-pentanoic acid;
(2R,4R)-2-Aminomethyl-5-cyclohexyl-4-methyl-pentanoic acid;
(2R,4R)-2-Aminomethyl-6-cyclopropyl-4-methyl-hexanoic acid;
(2R,4R)-2-Aminomethyl-6-cyclobutyl-4-methyl-hexanoic acid;
(2R,4R)-2-Aminomethyl-6-cyclopentyl-4-methyl-hexanoic acid;
(2R,4R)-2-Aminomethyl-6-cyclohexyl-4-methyl-hexanoic acid;
(2R,4R)-2-Aminomethyl-7-cyclopropyl-4-methyl-heptanoic acid;
(2R,4R)-2-Aminomethyl-7-cyclobutyl-4-methyl-heptanoic acid;
(2R,4R)-2-Aminomethyl-7-cyclopentyl-4-methyl-heptanoic acid;
(2R,4R)-2-Aminomethyl-7-cyclohexyl-4-methyl-heptanoic acid;
(2R,4R)-2-Aminomethyl-8-cyclopropyl-4-methyl-octanoic acid;
(2R,4R)-2-Aminomethyl-8-cyclobutyl-4-methyl-octanoic acid;
(2R,4R)-2-Aminomethyl-8-cyclopentyl-4-methyl-octanoic acid; and
(2R,4R)-2-Aminomethyl-8-cyclohexyl-4-methyl-octanoic acid.

This invention also relates to compounds of the formula III

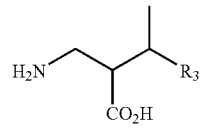

and their pharmaceutically acceptable salts, wherein $R_3$ is defined as for formula I above.

This invention also relates to compounds of the formula IV

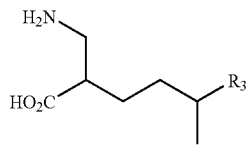

and their pharmaceutically acceptable salts, wherein $R_1$ and $R_3$ are defined as for compounds of the formula I above.

Other specific embodiments of this invention include the following compounds of the formula IV and their pharmaceutically acceptable salts:

2-Aminomethyl-6-cyclopropyl-5-methyl-hexanoic acid;
2-Aminomethyl-6-cyclobutyl-5-methyl-hexanoic acid;
2-Aminomethyl-6-cyclopentyl-5-methyl-hexanoic acid;
2-Aminomethyl-6-cyclohexyl-5-methyl-hexanoic acid;
2-Aminomethyl-7-cyclopropyl-5-methyl-heptanoic acid;
2-Aminomethyl-7-cyclobutyl-5-methyl-heptanoic acid;
2-Aminomethyl-7-cyclopentyl-5-methyl-heptanoic acid;
2-Aminomethyl-7-cyclohexyl-5-methyl-heptanoic acid;
2-Aminomethyl-8-cyclopropyl-5-methyl-octanoic acid;
2-Aminomethyl-8-cyclobutyl-5-methyl-octanoic acid;
2-Aminomethyl-8-cyclopentyl-5-methyl-octanoic acid;
2-Aminomethyl-8-cyclohexyl-5-methyl-octanoic acid;
2-Aminomethyl-5-methyl-heptanoic acid;
2-Aminomethyl-5-methyl-octanoic acid;
2-Aminomethyl-5-methyl-heptanoic acid;
2-Aminomethyl-5-methyl-nonanoic acid;
(2R,6S)-2-Aminomethyl-6-cyclopropyl-5-methyl-hexanoic acid;

(2R,6S)-2-Aminomethyl-6-cyclobutyl-5-methyl-hexanoic acid;
(2R,6S)-2-Aminomethyl-6-cyclopentyl-5-methyl-hexanoic acid;
(2R,6S)-2-Aminomethyl-6-cyclohexyl-5-methyl-hexanoic acid;
(2R,6S)-2-Aminomethyl-7-cyclopropyl-5-methyl-heptanoic acid;
(2R,6S)-2-Aminomethyl-7-cyclobutyl-5-methyl-heptanoic acid;
(2R,6S)-2-Aminomethyl-7-cyclopentyl-5-methyl-heptanoic acid;
(2R,6S)-2-Aminomethyl-7-cyclohexyl-5-methyl-heptanoic acid;
(2R,6S)-2-Aminomethyl-8-cyclopropyl-5-methyl-octanoic acid;
(2R,6S)-2-Aminomethyl-8-cyclobutyl-5-methyl-octanoic acid;
(2R,6S)-2-Aminomethyl-8-cyclopentyl-5-methyl-octanoic acid;
(2R,6S)-2-Aminomethyl-8-cyclohexyl-5-methyl-octanoic acid;
(2R,6S)-2-Aminomethyl-5-methyl-heptanoic acid;
(2R,6S)-2-Aminomethyl-5-methyl-octanoic acid;
(2R,6S)-2-Aminomethyl-5-methyl-heptanoic acid;
(2R,6S)-2-Aminomethyl-5-methyl-nonanoic acid;
(2R,6R)-2-Aminomethyl-6-cyclopropyl-5-methyl-hexanoic acid;
(2R,6R)-2-Aminomethyl-6-cyclobutyl-5-methyl-hexanoic acid;
(2R,6R)-2-Aminomethyl-6-cyclopentyl-5-methyl-hexanoic acid;
(2R,6R)-2-Aminomethyl-6-cyclohexyl-5-methyl-hexanoic acid;
(2R,6R)-2-Aminomethyl-7-cyclopropyl-5-methyl-heptanoic acid;
(2R,6R)-2-Aminomethyl-7-cyclobutyl-5-methyl-heptanoic acid;
(2R,6R)-2-Aminomethyl-7-cyclopentyl-5-methyl-heptanoic acid;
(2R,6R)-2-Aminomethyl-7-cyclohexyl-5-methyl-heptanoic acid;
(2R,6R)-2-Aminomethyl-8-cyclopropyl-5-methyl-octanoic acid;
(2R,6R)-2-Aminomethyl-8-cyclobutyl-5-methyl-octanoic acid;
(2R,6R)-2-Aminomethyl-8-cyclopentyl-5-methyl-octanoic acid;
(2R,6R)-2-Aminomethyl-8-cyclohexyl-5-methyl-octanoic acid;
(2R,6R)-2-Aminomethyl-5-methyl-heptanoic acid;
(2R,6R)-2-Aminomethyl-5-methyl-octanoic acid;
(2R,6R)-2-Aminomethyl-5-methyl-heptanoic acid; and
(2R,6R)-2-Aminomethyl-5-methyl-nonanoic acid.

This invention also relates to a pharmaceutical composition comprising a therapeutically effective amount of a compound of the formula I, IA, IA-1, IA-2, IB, IC, II, IIA, III, or IV, or a pharmaceutically acceptable salt thereof, and a pharmaceutically acceptable carrier.

This invention also relates to a method of treating a disorder or condition selected from epilepsy, faintness attacks, fibromyalgia, hypokinesia, cranial disorders, hot flashes, essential tremor, chemical dependencies and addictions, (e.g., dependencies on or addictions to alcohol, amphetamines (or amphetamine-like substances) caffeine, cannabis, cocaine, heroin, hallucinogens, tobacco, inhalants and aerosol propellants, nicotine, opioids, phenylglycidine derivatives, sedatives, hypnotics, benzodiazepines and other anxiolytics), and withdrawal symptoms associated with such depencies or addictions, addictive behaviors such as gambling; migraine, spasticity, arthritis, irritable bowel syndrome (IBS), chronic pain, acute pain, neuropathic pain, vascular headache, sinus headache, inflammatory disorders (e.g., rheumatoid arthritis, osteoarthritis, psoriasis) diuresis, premenstrual syndrome, premenstrual dysphoric disorder, tinnitis, and gastric damage in a mammal, including a human, comprising administering to a mammal in need of such treatment a therapeutically effective amount of a compound of the formula I, IA, IA-1, IA-2, IB, IC, II, IIA, III, or IV, or a pharmaceutically acceptable salt thereof.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia, such as those that occur in patients undergoing carotid endarterectomy or other cerebrovascular or vascular surgical procedures, or diagnostic vascular procedures including cerebral angiography and the like.

Compounds of the formulas I, IA, IA-1, IA-2, IB, IC, II, IIA, III, and IV, are also useful in the treatment of head trauma, spinal cord trauma, or injury from general anoxia, hypoxia, hypoglycemia, hypotension as well as similar injuries seen during procedures from embole, hyperfusion, and hypoxia. They are also useful in preventing neuronal damage that occurs during cardiac bypass surgery, in incidents of intracranial hemorrhage, in perinatal asphyxia, in cardiac arrest, and status epilepticus.

This invention also relates to a method of treating a disorder or condition selected from the group consisting of delerium, dementia, and amnestic and other cognitive or neurodegenerative disorders, such as Parkinson's disease (PD), Huntington's disease (HD), Alzheimer's disease, senile dementia, dementia of the Alzheimer's type, memory disorder, vascular dementia, and other dementias, for example, due to HIV disease, head trauma, Parkinson's disease, Huntington's disease, Pick's disease, Creutzfeldt-Jakob disease, or due to multiple aetiologies; movement disorders such as akinesias, dyskinesias, including familial paroxysmal dyskinesias, spasticities, Tourette's syndrome, Scott syndrome, PALSYS and akinetic-rigid syndrome; extra-pyramidal movement disorders such as medication-induced movement disorders, for example, neuroleptic-induced Parkinsonism, neuroleptic malignant syndrome, neuroleptic-induced acute dystonia, neuroleptic-induced acute akathisia, neuroleptic-induced tardive dyskinesia and medication-induced postural tremour; Down's syndrome; demyelinating diseases such as multiple sclerosis (MS) and amylolateral sclerosis (ALS), peripheral neuropathy, for example diabetic and chemotherapy-induced-neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema in a mammal, including a human, comprising administering to said mammal an amount of a compound of the formula I, IA, IA-1, IA-2, IB, IC, II, IIA, III, or IV, or a pharmaceutically acceptable salt thereof, that is effective in treating such disorder or condition.

Pain refers to acute as well as chronic pain. Acute pain is usually short-lived and is associated with hyperactivity of the sympathetic nervous system. Examples are postoperative pain and allodynia. Chronic pain is usually defined as pain persisting from 3 to 6 months and includes somatogenic pain and psychogenic pain. Other pain is nociceptive.

Examples of the types of pain that can be treated with the compounds of formulas I, IA, IA-1, IA-2, IB, IC, II, IIA, III, and IV of the present invention and their pharmaceutically acceptable salts include pain resulting from soft tissue and peripheral damage, such as acute trauma, pain associated with osteoarthritis and rheumatoid arthritis, musculo-skeletal pain, such as pain experienced after trauma; spinal pain, dental pain, myofascial pain syndromes, episiotomy pain, and pain resulting from burns; deep and visceral pain, such as heart pain, muscle pain, eye pain, orofacial pain, for example, odontalgia, abdominal pain, gynaecological pain, for example, dysmenorrhoea, labour pain and pain associated with endometriosis; pain associated with nerve and root damage, such as pain associated with peripheral nerve disorders, for example, nerve entrapment and brachial plexus avulsions, amputation, peripheral neuropathies, tic douloureux, a typical facial pain, nerve root damage, trigeminal neuralgia, neuropathic lower back pain, HIV related neuropathic pain, cancer related neuropathic pain, diabetic neuropathic pain, and arachnoiditis; neuropathic and non-neuropathic pain associated with carcinoma, often referred to as cancer pain; central nervous system pain, such as pain due to spinal cord or brain stem damage; lower back pain; sciatica; phantom limb pain, headache, including migraine and other vascular headaches, acute or chronic tension headache, cluster headache, temperomandibular pain and maxillary sinus pain; pain resulting from ankylosing spondylitis and gout; pain caused by increased blader contractions; post operative pain; scar pain; and chronic non-neuropathic pain such as pain associated with fibromyalgia, HIV, rheumatoid and osteoarthritis, anthralgia and myalgia, sprains, strains and trauma such as broken bones; and post surgical pain.

Still other pain is caused by injury or infection of peripheral sensory nerves. It includes, but is not limited to pain from peripheral nerve trauma, herpes virus infection, diabetes mellitus, fibromyalgia, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, a typical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

The compounds of the invention are also useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

This invention also relates to a method of treating a disorder or condition selected from the group consisting of mood disorders, such as depression, or more particularly, depressive disorders, for example, single episodic or recurrent major depressive disorders, dysthymic disorders, depressive neurosis and neurotic depression, melancholic depression, including anorexia, weight loss, insomnia, early morning waking and psychomotor retardation, a typical depression (or reactive depression), including increased appetite, hypersomnia, psychomotor agitation or irritability, seasonal affective disorder and pediatric depression; or bipolar disorders or manic depression, for example, bipolar I disorder, bipolar II disorder and cyclothymic disorder; conduct disorder and disruptive behavior disorder; anxiety disorders, such as panic disorder with or without agoraphobia, agoraphobia without history of panic disorder, specific phobias, for example, specific animal phobias, social anxiety, social phobia, obsessive-compulsive disorder, stress disorders, including post-traumatic stress disorder and acute stress disorder, and generalized anxiety disorders; borderline personality disorder; schizophrenia and other psychotic disorders, for example, schizophreniform disorders, schizoaffective disorders, delusional disorders, brief psychotic disorders, shared psychotic disorders, psychotic disorders with delusions or hallucinations, psychotic episodes of anxiety, anxiety associated with psychosis, psychotic mood disorders such as severe major depressive disorder; mood disorders associated with psychotic disorders such as acute mania and depression associated with bipolar disorder, mood disorders associated with schizophrenia; behavioral disturbances associated with mental retardation, autistic disorder, and conduct disorder in a mammal, including a human, comprising administering to said mammal an amount of a compound of the formula I, IA, IA-1, IA-2, IB, IC, II, IIA, III, or IV, or a pharmaceutically acceptable salt thereof, that is effective in treating such disorder or condition.

The compounds of the invention are also useful in the treatment of sleep disorders. Sleep disorders are disturbances that affect the ability to fall and/or stay asleep, that involves sleeping too much, or that result in abnormal behavior associated with sleep. The disorders include, for example, insomnia, drug-associated sleeplessness, hypersomnia, narcolepsy, sleep apnea syndromes, and parasomnias.

This invention also relates to a method of treating a disorder or condition selected from the group consisting of sleep disorders (e.g., insomnia, drug-associated sleeplessness, REM sleep disorders, hypersomnia, narcolepsy, sleep-wake cycle disorders, sleep apnea syndromes, parasomnias, and sleep disorders associated with shift work and irregular work hours) a mammal, including a human, comprising administering to said mammal an amount of a compound of the formula I, IA, IA-1, IA-2, IB, IC, II, IIA, III, or IV, or a pharmaceutically acceptable salt thereof, that is effective in treating such disorder or condition.

Compounds of formulas I, IA, IA-1, IA-2, IB, IC, II, IIA, III, and IV contain at least one chiral center and therefore may exist in different enantiomeric and diastereomeric forms. This invention relates to all optical isomers and all stereoisomers of compounds of the formulas I, IA, IA-1, IA-2, IB, IC, II, IIA, III, and IV, both as racemic mixtures and as individual enantiomers and diastereoisomers of such compounds, and mixtures thereof, and to all pharmaceutical compositions and methods of treatment defined above that contain or employ them, respectively. Individual isomers can be obtained by known methods, such as optical resolution, optically selective reaction, or chromatographic separation in the preparation of the final product or its intermediate. Individual enantiomers of the compounds of this invention may have advantages, as compared with the racemic mixtures of these compounds, in the treatment of various disorders or conditions.

The present invention also includes isotopically labelled compounds, which are identical to those recited in formulas I, IA, IA-1, IA-2, IB, IC, II, IIA, III, and IV, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14 i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The term "alkyl", as used herein, unless otherwise indicated, includes saturated monovalent hydrocarbon radicals having straight, branched or cyclic moieties or combinations thereof. Examples of "alkyl" groups include, but are not limited to, methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy", as used herein, unless otherwise indicated, means "alkyl-O—", wherein "alkyl" is as defined above. Examples of "alkoxy" groups include, but are not limited to, methoxy, ethoxy, propoxy, butoxy and pentoxy.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

Because amino acids are amphoteric, pharmacologically compatible salts can be salts of appropriate inorganic or organic acids, for example, hydrochloric, sulphuric, phosphoric, acetic, oxalic, lactic, citric, malic, salicylic, malonic, maleic, succinic, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethylammonium ion.

The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form.

A prodrug is a drug that has been chemically modified and may be biologically inactive at its site of action, but which may be degraded or modified by one or more enzymatic or other in vivo processes to the parent bioactive form.

This chemically modified drug, or prodrug, should have a different pharmacokinetic profile than the parent drug, enabling easier absorption across the mucosal epithelium, better salt formulation and/or solubility, improved systemic stability (for an increase in plasma half-life, for example). These chemical modifications may be 1) ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.
2) peptides which may be recognized by specific or non-specific proteinases. A peptide may be coupled to the drug molecule via amide bond formation with the amine or carboxylic acid moiety of the drug molecule by known means.
3) derivatives that accumulate at a site of action through membrane selection of a prodrug form or modified prodrug form,
4) any combination of 1 to 3.

Current research in animal experiments has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug upon hydrolysis.

"Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Prodrugs of compounds of formulas I, IA, IA-1, IA-2, IB, IC, II, IIA, III, and IV are included within the scope of this invention. Prodrugs and soft drugs are known in the art (Palomino E., *Drugs of the Future*, 1990;15(4):361–368). The last two citations are hereby incorporated by reference.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

DETAILED DESCRIPTION OF THE INVENTION

The compounds of this invention can be prepared as described below. In the reaction schemes and discussion that follow, structural formulas I, IA, IA-1, IA-2, IB, IC, II, IIA, III, and IV, and the radicals $R_1$, $R_2$, $R_3$, $R_4$, $R_5$ and $R_6$, unless otherwise indicated, are defined as above.

Diverse methods exist for the preparation of chiral and racemic β-amino acids. Such methods can be found in "Enantioselective Synthesis of β-Amino Acids", Juaristi, Eusebio; Editor. USA, 1997, Wiley-VCH, New York, N.Y.

The methods described below are illustrative of methods that can be utilized for the preparation of such compounds but are not limiting in scope.

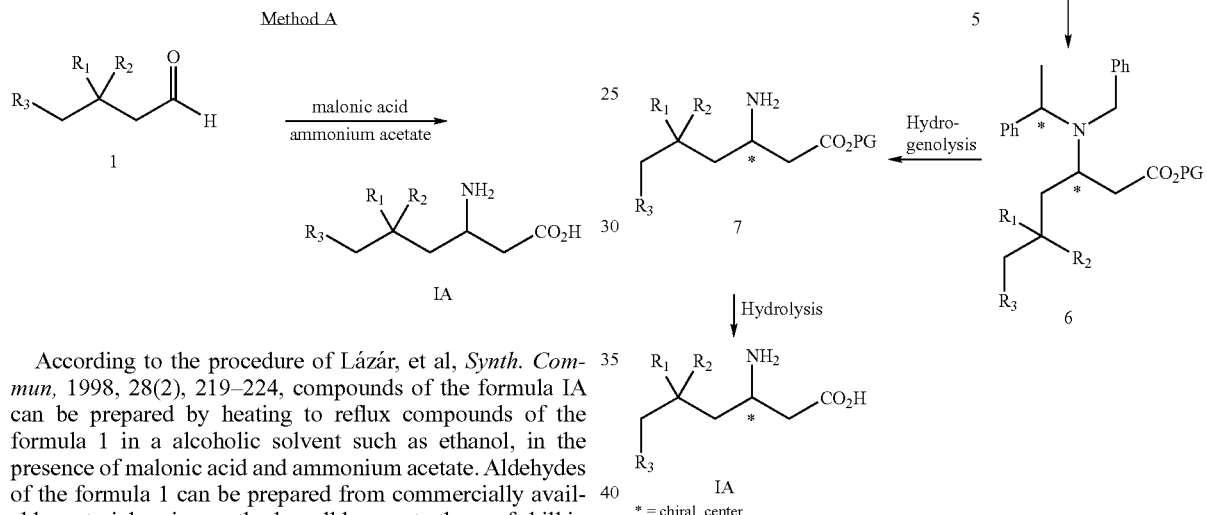

According to the procedure of Lázár, et al, *Synth. Commun*, 1998, 28(2), 219–224, compounds of the formula IA can be prepared by heating to reflux compounds of the formula 1 in a alcoholic solvent such as ethanol, in the presence of malonic acid and ammonium acetate. Aldehydes of the formula 1 can be prepared from commercially available materials using methods well known to those of skill in the art.

Compounds that can be made by the above method include, but are not limited to the following:

3-Amino-6-cyclopropyl-5-methyl-hexanoic acid;
3-Amino-6-cyclobutyl-5-methyl-hexanoic acid;
3-Amino-6-cyclopentyl-5-methyl-hexanoic acid;
3-Amino-6-cyclohexyl-5-methyl-hexanoic acid;
3-Amino-7-cyclopropyl-5-methyl-heptanoic acid;
3-Amino-7-cyclobutyl-5-methyl-heptanoic acid;
3-Amino-7-cyclopentyl-5-methyl-heptanoic acid;
3-Amino-7-cyclohexyl-5-methyl-heptanoic acid;
3-Amino-8-cyclopropyl-5-methyl-octanoic acid
3-Amino-8-cyclobutyl-5-methyl-octanoic acid;
3-Amino-8-cyclopentyl-5-methyl-octanoic acid;
3-Amino-8-cyclohexyl-5-methyl-octanoic acid;
3-Amino-6-cyclopropyl-5,5-dimethyl-hexanoic acid;
3-Amino-6-cyclobutyl-5,5-dimethyl-hexanoic acid;
3-Amino-6-cyclopentyl-5,5-dimethyl-hexanoic acid;
3-Amino-6-cyclohexyl-5,5-dimethyl-hexanoic acid;
3-Amino-7-cyclopropyl-5,5-dimethyl-heptanoic acid;
3-Amino-7-cyclobutyl-5,5-dimethyl-heptanoic acid;
3-Amino-7-cyclopentyl-5,5-dimethyl-heptanoic acid; and
3-Amino-7-cyclohexyl-5,5-dimethyl-heptanoic acid.

The use of chiral amine additions to α,β-unsaturated systems as a synthetic approach to β-amino acids, as illustrated in Method B above, has been described previously (see, e.g., S. G. Davies et al, *J. Chem. Soc. Chem. Commun*, 1153, 1993; S. G. Davies, *Synlett*, 1994, 117; Ishikawa et al, *Synlett*, 1998, 1291; Hawkins, *J. Org. Chem.*, 1985, 51, 2820). Referring to Method B above, compounds of the formula IA can be prepared from the corresponding compounds of the formula 7, wherein PG represents a suitable ester protecting group that can be removed by hydrolysis or hydrogenolysis, using conditions well known to those of skill in the art. (See T. W. Greene and P. G. M. Wuts., "*Protective groups in organic synthesis*", Wiley, 1991 for a detailed description for the formation and removal of suitable protecting groups). For example, this reaction can be conducted under hydrolytic conditions by treatment with an appropriate acid, such as hydrochloric acid or sulfuric acid, at a temperature from about room temperature to about the reflux temperature of the reaction mixture, preferably at the reflux temperature, or by treatment with an appropriate inorganic base, such as sodium hydroxide, potassium hydroxide, or lithium hydroxide, preferably sodium hydroxide, at a temperature from about room temperature to about the reflux temperature, preferably at about room temperature. This reaction is preferably carried out using hydrochloric acid at the reflux temperature. When PG is t-butyl, however, the reaction is preferably carried out in trifluoroacetic acid (TFA). When PG is a basic group, the hydrolysis can be carried out under basic conditions, using methods well known to those of skill in the art, for example, using sodium or potassium hydroxide.

Compounds of the formula 7 can be prepared from the corresponding compounds of the formula 6 using hydrogenolysis conditions that are well known to those of skill in the art. For example, this reaction can be carried out by treating the compounds of formula 6 with a palladium metal catalyst, such as, for example, palladium hydroxide on carbon, or palladium on carbon, or with Raney Nickel, in a solvent such as, for example, methanol, ethanol or tetrahydrofuran, under an atmosphere of hydrogen (between about 1 and 5 atmospheres of pressure) to give the desired compound of formula 7. Preferably, the reaction is carried out using palladium on carbon in ethanol under about 1 atmosphere of hydrogen.

Compounds of the formula 6 can be prepared by treating the corresponding compounds of formula 4 with an appropriate amine such as (R)-(+)-N-benzyl-α-methylbenzylamine, (S)-(-)-N-benzyl-α-methylbenzylamine after treatment with an appropriate base such as lithium diisopropylamide, n-butyl lithium, or lithium or potassium bis(trimethylsilyl)amide, in a solvent such as ethyl ether, or, preferably, tetrahydrofuran (THF), at a temperature from about −80° C. to about 25° C., and then adding the appropriate compound of formula formula 4. The stereochemistry about the nitrogen of the amine will determine the stereochemistry about the nitrogen of the final product. Preferably, this reaction is carried out using either (R)-(+)-N-benzyl-α-methylbenzylamine, (S)-(-)-N-benzyl-α-methylbenzylamine, after deprotonation with n-butyl-lithium in tetrahydrofuran, at a temperature of about −78° C., according to method described by Bull, Steven D.; Davies, Stephen G.; and Smith, Andrew D, *J. Chem. Soc., Perkin Trans.* 1, 2001, 22, 2931–2938. Preferably, this reaction is carried out using either (R)-(+)-N-benzyl-α-methylbenzylamine, or (S)-(-)-N-benzyl-α-methylbenzylamine, after deprotonation with n-butyl-lithium in tetrahydrofuran, at a temperature of about −78° C., according to method described by Bull, Steven D.; Davies, Stephen G.; and Smith, Andrew D, *J. Chem. Soc., Perkin Trans.* 1, 2001, 22, 2931–2938.

Compounds of the formula 4 can be prepared from the corresponding compounds of formula 3 by treating them with an appropriate phosphonate ester in the presence of a suitable base such as sodium hydride, lithium diisopropylamide, or triethyl amine and either lithium chloride or lithium bromide, in a solvent such as ether or THF. Preferably, the compound of formula 3 is reacted with a phosphonate ester (ALK=methyl, ethyl, isopropyl, benzyl or the like) in the presence of lithium bromide and triethylamine in tetrahydrofuran at about room temperature. Compounds of the formula 3 can be prepared from commercially available materials using methods well known to those of skill in the art. It will be appreciated that compounds of the formula 3 may possess one or more stereogenic centers. Using the above described method, compounds with specific stereochemical configurations can be prepared.

Compounds that can be made by this method include, but are not limited to the following:
(3S,5R)-3-Amino-6-cyclopropyl-5-methyl-hexanoic acid;
(3S,5R)-3-Amino-6-cyclobutyl-5-methyl-hexanoic acid;
(3S,5R)-3-Amino-6-cyclopentyl-5-methyl-hexanoic acid;
(3S,5R)-3-Amino-6-cyclohexyl-5-methyl-hexanoic acid;.
(3S,5R)-3-Amino-8-cyclopropyl-5-methyl-octanoic acid;
(3S,5R)-3-Amino-8-cyclobutyl-5-methyl-octanoic acid;
(3S,5R)-3-Amino-8-cyclopentyl-5-methyl-octanoic acid;
(3S,5R)-3-Amino-8-cyclohexyl-5-methyl-octanoic acid;
(3S,5S)-3-Amino-6-cyclopropyl-5-methyl-hexanoic acid;
(3S,5S)-3-Amino-6-cyclobutyl-5-methyl-hexanoic acid;
(3S,5S)-3-Amino-6-cyclopentyl-5-methyl-hexanoic acid;
(3S,5S)-3-Amino-6-cyclohexyl-5-methyl-hexanoic acid;
(3S,5S)-3-Amino-8-cyclopropyl-5-methyl-octanoic acid;
(3S,5S)-3-Amino-8-cyclobutyl-5-methyl-octanoic acid;
(3S,5S)-3-Amino-8-cyclopentyl-5-methyl-octanoic acid;
(3S,5S)-3-Amino-8-cyclohexyl-5-methyl-octanoic acid;
(3S)-3-Amino-6-cyclopropyl-5,5-dimethyl-hexanoic acid;
(3S)-3-Amino-6-cyclobutyl-5,5-dimethyl-hexanoic acid;
(3S)-3-Amino-6-cyclopentyl-5,5-dimethyl-hexanoic acid;
(3S)-3-Amino-6-cyclohexyl-5,5-dimethyl-hexanoic acid;
(3S)-3-Amino-7-cyclopropyl-5,5-dimethyl-heptanoic acid;
(3S)-3-Amino-7-cyclobutyl-5,5-dimethyl-heptanoic acid;
(3S)-3-Amino-7-cyclopentyl-5,5-dimethyl-heptanoic acid; and
(3S)-3-Amino-7-cyclohexyl-5,5-dimethyl-heptanoic acid.

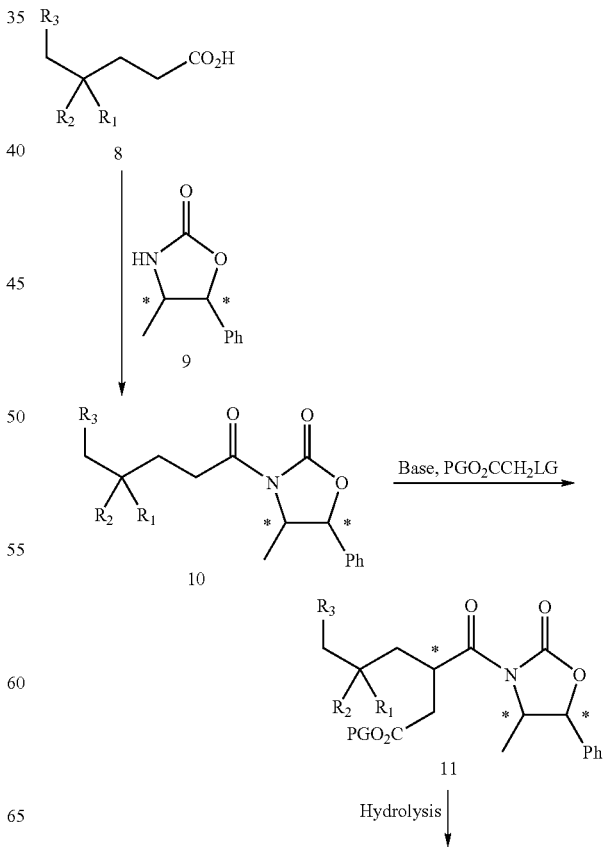

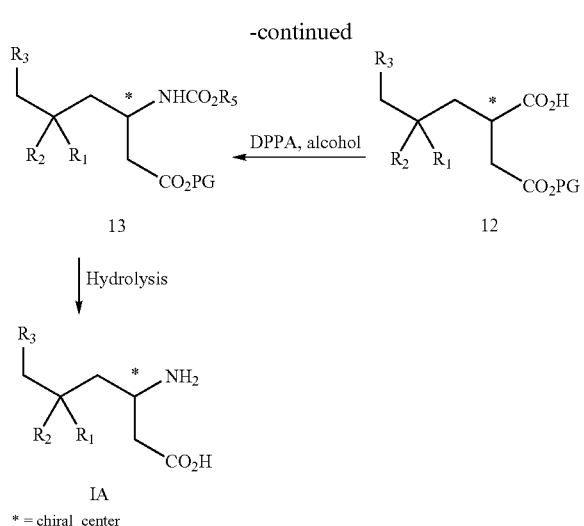

* = chiral center

The diastereoalkylation of imides such as those of formula 10 to afford chiral succinate analogs such as those of formula 11 has been previously described as an approach to preparing β-amino acids (see, e.g., Evans et al, *J. Org. Chem.*, 1999, 64, 6411; Sibi and Deshpande, *J. Chem. Soc. Perkin Trans 1.*, 2000, 1461; Arvanitis et al, *J. Chem. Soc. Perkin Trans 1.*, 1998, 521).

Compounds of structure 11 can be prepared from compounds of structure 10 in the presence of a suitably derived ester (PG as defined above, LG=Br or I or Cl) such as, for example, t-butyl bromoacetate, benzyl bromoacetate with an organometallic base such as, for example, lithium diisopropylamide or lithium bis(trimethylsilyl)amide or sodium bis(trimethylsilyl)amide and the like in a solvent such as, for example, tetrahydrofuran, ether, and the like. The reaction can be carried out using sodium bis(trimethylsilyl)amide in tetrahydrofuran at −78° C. and treatment of the resultant anion intermediate with t-butyl bromoacetate at −78° C. to −30° C.

Compounds of the formula 12 can be prepared by hydrolysing the corresponding compounds of formula 11 in the presence of lithium hydroxide and hydrogen peroxide in a solvent such as water or THF, at a temperature from about 0° C. to about room temperature. Preferably, this reaction is carried out using hydrogen peroxide and lithium hydroxide in aqueous tetrahydrofuran at about 0° C. according to the method described in the literature (See Yuen P-W., Kanter G. D., Taylor C. P., and Vartanian M. G., *Bioorganic and Medicinal Chem. Lett.*, 1994;4(6):823–826).

Treatment of a compound of the formula 12 with diphenylphosphorylazide in the presence of a suitable alcohol such as t-butanol, benzyl alcohol or p-methoxybenzyl alcohol, in a suitable solvent such as toluene, benzene, or THF, at a temperature from about 50° C. to about the reflux temperature of the reation mixture yields the corresponding compound of formula 13 wherein $R_5$ is methyl, ethyl, t-butyl, benzyl, or p-methoxybenzyl. $R_5$ is dependent on the choice of the alcohol used. Preferably, this reaction is carried out using a toluene solvent in the presence of p-methoxybenzyl alcohol under refluxing conditions.

Compounds of the formula 13 can be converted into the desired compounds of formula IA by hydrolysis or hydrogenolysis, using conditions well known to those of skill in the art. (See T. W. Greene and P. G. M. Wuts., *"Protective groups in organic synthesis"*, Wiley, 1991 for a detailed description for the formation and removal of suitable protecting groups). For example, this reaction can be conducted under hydrolytic conditions by treatment with an appropriate acid, such as hydrochloric acid or sulfuric acid, at a temperature from about room temperature to about the reflux temperature of the reaction mixture, preferably at the reflux temperature, or by treatment with an appropriate inorganic base, such as sodium hydroxide, potassium hydroxide, or lithium hydroxide, preferably sodium hydroxide, at a temperature from about room temperature to about the reflux temperature, preferably at about room temperature. This reaction is preferably carried out using hydrochloric acid at the reflux temperature. When PG is t-butyl, however, the reaction is preferably carried out in trifluoroacetic acid (TFA). When PG is a basic group, the hydrolysis can be carried out under basic conditions, using methods well known to those of skill in the art, for example, using sodium or potassium hydroxide.

Compounds of the formula 10 can be prepared by treating the corresponding compounds of formula 8 with an amine base such as triethylamine, in the presence of trimethylacetylchloride, in an ethereal solvent such as THF, and then treating the intermediates formed by this reaction [in situ] with a chiral oxazolidinone of the formula 9. Examples of other oxazolidonones that can be used in this method are: (4S)-(−)-4-isopropyl-2-oxazolidinone; (S)-(−)-4-benzyl-2-oxazolidinone; (4S,5R)-(−)-4-methyl-5-phenyl-2-oxazolidinone; (R)-(+)-4-benzyl-2-oxazolidinone, (S)-(+)-4-phenyl-2-oxazolidinone; (R)-(−)-4-phenyl-2-oxazolidinone; (R)-4-isopropyl-2-oxazolidinone; and (4R,5S)-(+)-4-methyl-5-phenyl-2-oxazolidinone)) and lithium chloride. Preferably, this reaction is carried out by treating an acid of the formula 8 with trimethylacetylchloride and triethylamine in tetrahydrofuran at about −20° C., followed by treatment of the intermediate formed in such reaction with an oxazolidinone of the formula 9 and lithium chloride at about room temperature according to literature procedures (See Ho G-J. and Mathre D. J., *J. Org. Chem.*, 1995;60:2271–2273).

Alternatively, compounds of the formula 10 can be prepared by treating the corresponding compounds of the formula 9 with the acid chloride derived from treatment of the corresponding compound of the formula 8 with oxalyl chloride, in a solvent such as dichloromethane, in the presence of dimethylformamide (DMF). Acids of the formula 8 can be prepared from commercially available materials using methods well known to those of skill in the art. These acids may possess one or more chiral centers. The use of citronellyl bromide and citronellol in the synthesis of such acids is described in Examples 1, 2 and 3 of this application.

Compounds that can be prepared by the above Method C include, but are not limited to the following:
(3S,5R)-3-Amino-5-methyl-heptanoic acid;
(3S,5R)-3-Amino-5-methyl-octanoic acid;
(3S,5R)-3-Amino-5-methyl-nonanoic acid;
(3S,5R)-3-Amino-5-methyl-decanoic acid;
(3S,5S)-3-Amino-5-methyl-heptanoic acid;
(3S,5S)-3-Amino-5-methyl-octanoic acid;
(3S,5S)-3-Amino-5-methyl-nonanoic acid;
(3S,5S)-3-Amino-5-methyl-decanoic acid;
(3S)-3-Amino-5,5-dimethyl-heptanoic acid;
(3S)-3-Amino-5,5-dimethyl-octanoic acid;
(3S)-3-Amino-5,5-dimethyl-nonanoic acid;
(3S)-3-Amino-5,5-dimethyl-decanoic acid;
(3S,5R)-3-Amino-7-cyclopropyl-5-methyl-heptanoic acid;
(3S,5R)-3-Amino-7-cyclobutyl-5-methyl-heptanoic acid;
(3S,5R)-3-Amino-7-cyclopentyl-5-methyl-heptanoic acid;
(3S,5R)-3-Amino-7-cyclohexyl-5-methyl-heptanoic acid;
(3S,5S)-3-Amino-7-cyclopropyl-5-methyl-heptanoic acid;
(3S,5S)-3-Amino-7-cyclobutyl-5-methyl-heptanoic acid;
(3S,5S)-3-Amino-7-cyclopentyl-5-methyl-heptanoic acid; and (3S,5S)-3-Amino-7-cyclohexyl-5-methyl-heptanoic acid.

Alternatively, referring to the reaction scheme (Method D) below, compounds of the formula 11 can be treated with an appropriate acid (for example, trifluoroacetic acid (TFA) when the t-butyl ester is used) to yield the corresponding compounds of formula 14, which can then be subjected to a Curtius rearrangement (where $R_5$ is defined as above) to yield the corresponding compounds of formula 15 (See Arvanitis et al, *J. Chem. Soc. Perkin Trans* 1., 1998, 521 for a description of this approach). Further hydrolysis of the imide group (to yield the corresponding compound of formula 16) and the carbamate group gives the desired β-amino acids of formula 11.

Compound 16 can be derived from compound 15 as described above for the conversion of compounds of the formula 11 into compounds of the formula 12. Compounds of the formula 17 can be prepared from corresponding compounds of the formula 16 through treatment with a strong acid, such as hydrochloric acid or the like, or a strong base, such as sodium or potassium hydroxide or, if $R_5$ is benzyl or p-methoxybenzyl, through hygrogenolytic conditions, using palladium on carbon in ethanol or THF under a hydrogen atmosphere. This approach, which preserves the stereochemistry about the chiral center in the compounds of formula 11, which is also present in the product of formula 11, is described in Example 4 of this application.

Compounds that can be made by this method include, but are not limited to the following:

(2R,4R)-2-Aminomethyl-4-methyl-hexanoic acid;
(2R,4R)-2-Aminomethyl-4-methyl-heptanoic acid;
(2R,4R)-2-Aminomethyl-4-methyl-octanoic acid;
(2R,4R)-2-Aminomethyl-4-methyl-nonanoic acid;
(2R,4R)-2-Aminomethyl-4-methyl-decanoic acid;
(2R,4S)-2-Aminomethyl-4-methyl-hexanoic acid;
(2R,4S)-2-Aminomethyl-4-methyl-heptanoic acid;
(2R,4S)-2-Aminomethyl-4-methyl-octanoic acid;
(2R,4S)-2-Aminomethyl-4-methyl-nonanoic acid;
(2R,4S)-2-Aminomethyl-4-methyl-decanoic acid;
(2R,4S)-2-Aminomethyl-6-cyclopropyl-4-methyl-hexanoic acid;
(2R,4S)-2-Aminomethyl-6-cyclobutyl-4-methyl-hexanoic acid;
(2R,4S)-2-Aminomethyl-6-cyclopentyl-4-methyl-hexanoic acid; and
(2R,4S)-2-Aminomethyl-6-cyclohexyl-4-methyl-hexanoic acid;

Other alternative approaches to synthesizing α-substituted β-amino acids that can be utilized for preparing the compounds of this invention include those described by Juaristi et al *Tetrahedron Asymm.*, 7, (8), 1996, 2233 and Seebach et al, *Eur. J. Org. Chem.*, 1999, 335, or by Arvanitis et al, *J. Chem. Soc. Perkin Trans* 1., 1998, 521, as shown in Method E below:

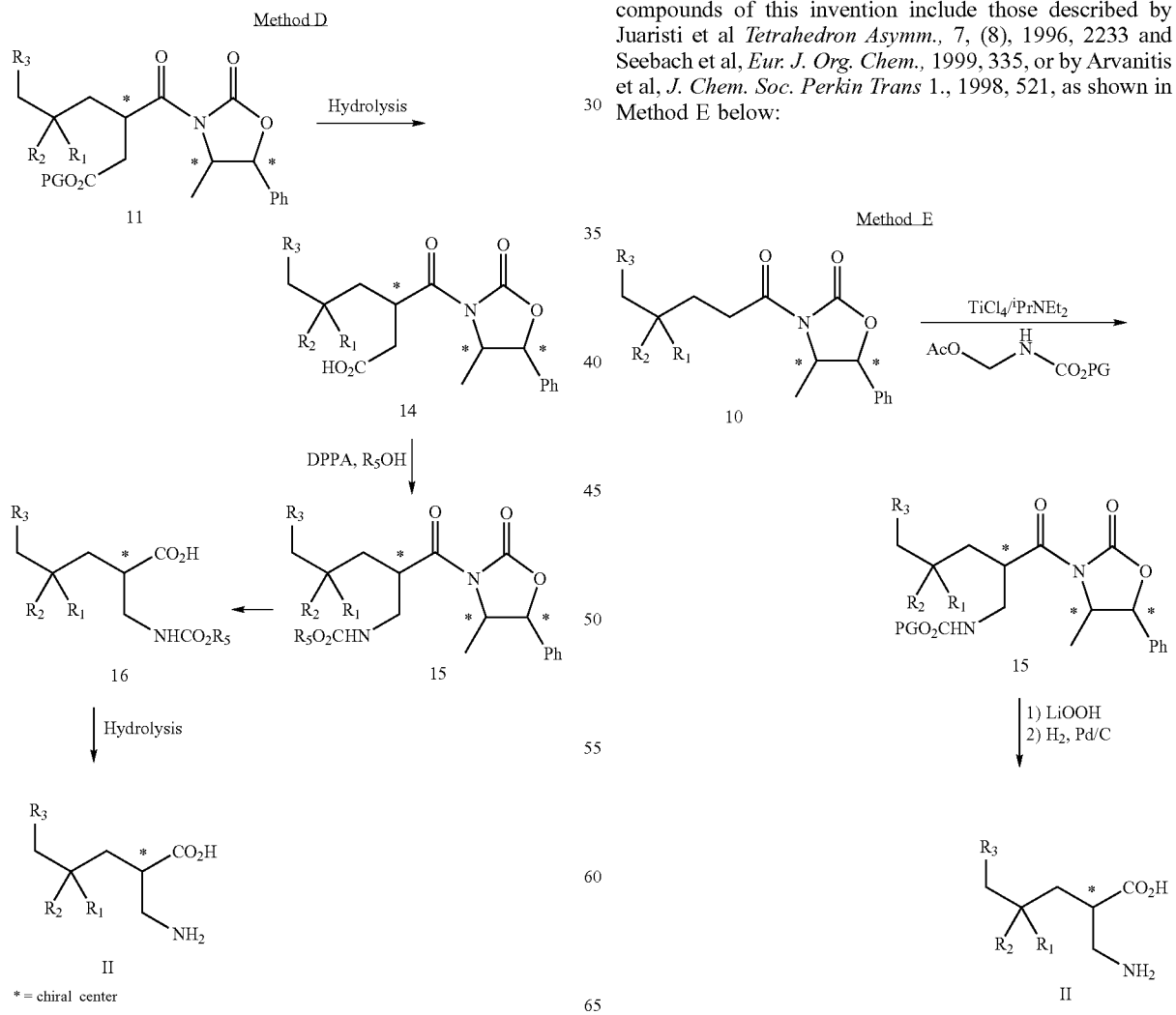

Method F below illustrates an alternate method of preparing compounds of the formula II.

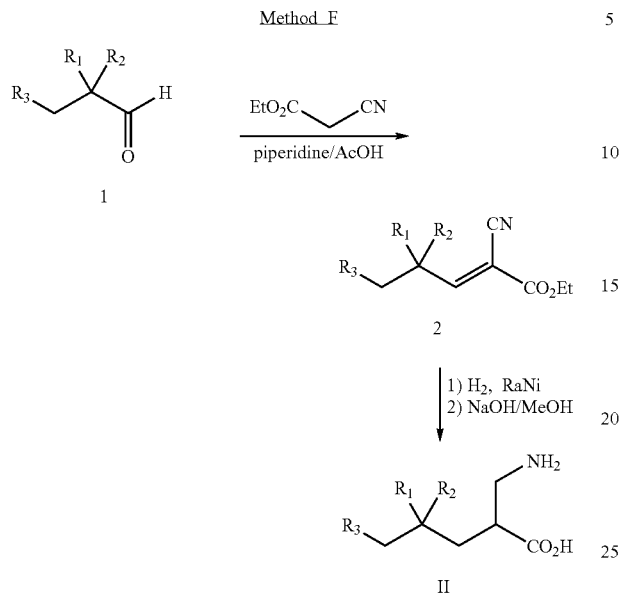

According to the procedure disclosed by Hoffmann-La Roche (FR 1377736 19641106), compounds of formula 3 can be prepared from unsaturated cyanoesters of formula 2 by reduction and hydrolysis. In turn, cyanoesters 2 can be prepared via Knoevenagel condensation of aldehydes 1 with cyanoacetic esters (e.g. Paine, J. B.; Woodward, R. B.; Dolphin, D., *J. Org. Chem.* 1976, 41, 2826). Aldehydes of the formula 1 can be prepared from commercially available materials by methods known to those skilled in the art.

Compounds of the formulas III and IV can be prepared using procedures analogous to those of Method F that will be obvious to those of skill in the art. When synthesizing a compound of the formula III, the starting material should be a compound similar to formula 1 in Method F, but wherein the hydrogen attached to the carbonyl group in formula 1 is replaced by a methyl group.

The use of chiral imines to afford β-amino acids, as illustrated in Method G below, has been described previously (see, e.g Tang, T. P.; Ellman, J. A. *J. Org. Chem.* 1999, 64, 12–13.).

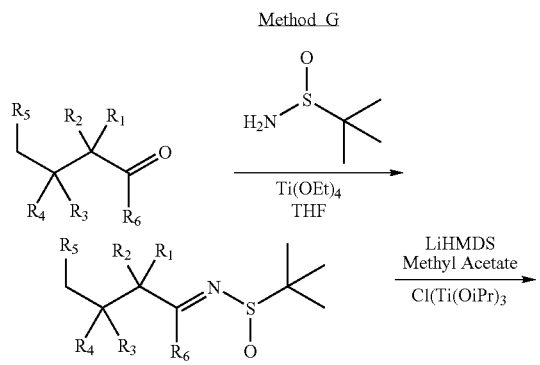

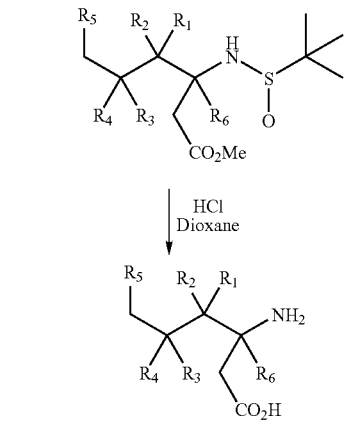

The final step in the above scheme is a hydrolysis of both the sulfonamide and ester groups. This reaction is generally carried out using a strong acid such as hydrochloric acid, hydrobromic acid or sulfuric acid, in a solvent such as water or dioxane or a mixture of water and dioxane, at a temperature from about 20° C. to about 50° C., preferably at about room temperature.

The preparation of compounds of this invention that are not specifically described in the foregoing experimental section can be accomplished using combinations of the reactions described above that will be apparent to those skilled in the art.

In each of the reactions discussed or illustrated above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of the formula 1 and the Group A compounds, and the intermediates shown in the above reaction schemes can be isolated and purified by conventional procedures, such as recrystallization or chromatographic separation.

The ability of compounds of the present invention to bind to the α2δ-subunit of a calcium channel can be determined using the following binding assay.

The radioligand binding assay using [$^3$H]-gabapentin and the α2δ-subunit derived from porcine brain tissue was used (See, Gee, Nicolas S et al. "The novel anticonvulsant drug, gabapentin (Neurontin), binds to the α2δ subunit of a calcium channel." *J. Biol. Chem.* (1996), 271(10), 5768–76). Compounds of the invention bind with nanomolar to micromolar affinity for the α2δ protein. For example, R-3-amino-5,9-dimethyl-decanoic acid binds with 527 nM affinity to the α2δ protein, (3S,5S)-3-amino-5-methyl-octanoic acid binds with 1 uM affinity, (2R,4R)-2-Aminomethyl-4-methyl-heptanoic acid binds with 29 nM affinity, 2-Aminomethyl-4,4-dimethyl-heptanoic acid binds with 83 nM affinity.

The In vivo activity of compounds of this invention can be determined in animal models of hyperalgesia (See Sluka, K., et al. 2001, "Unilateral Intramuscular Injections Of Acidic Saline Produce A Bilateral, Long-Lasting Hyperalgesia", *Muscle Nerve* 24: 37–46; Dixon, W., 1980, "Efficient analysis of experimental observations". *Ann Rev Pharmacol Toxicol* 20:441–462; Randall L. O. and Selitto J. J., "A Method For Measurement Of Analgesic Activity On Inflamed Tissue," *Arch. Int. Pharmacodyn,*

1957;4:409–419; Hargreaves K., Dubner R., Brown F., Flores C., and Joris J. "A New And Sensitive Method For Measuring Thermal Nociception In Cutaneous Hyperalgesia". *Pain.* 32:77–88, 1988.), anxiety (Vogel J R, Beer B, and Clody D E, "A Simple And Reliable Conflict Procedure For Testing Anti-Anxiety Agents", *Psychopharmacologia* 21:1–7, 1971), The compounds of the present invention, and their pharmaceutically acceptable salts, can be administered to mammals via either the oral, parenteral (such as subcutaneous, intravenous, intramuscular, intrasternal and infusion techniques), rectal, buccal or intranasal routes.

The novel compounds of the present invention may be administered alone or in combination with pharmaceutically acceptable carriers or diluents by any of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, suppositories, jellies, gels, pastes, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the weight ratio of the novel compounds of this invention to the pharmaceutically acceptable carrier will be in the range from about 1:6 to about 2:1, and preferably from about 1:4 to about 1:1.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

For intranasal administration or administration by inhalation, the novel compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch. Formulations of the active compounds of this invention for treatment of the conditions referred to above in the average adult human are preferably arranged so that each metered dose or "puff" of aerosol contains 20 μg to 1000 μg of active compound. The overall daily dose with an aerosol will be within the range 100 μg to 10 mg. Administration may be several times daily, for example 2, 3, 4 or 8 times, giving for example, 1, 2 or 3 doses each time.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of formula I, IA, IA-1, IA-2, IB, IC, II, IIA, III, or IV or a corresponding pharmaceutically acceptable salt of such compound.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material. In powders, the carrier is a finely divided solid which is in a mixture with the finely divided active component. In tablets, the active component is mixed with the carrier having the necessary binding, properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.01 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.1 mg to about 1 g daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following Examples illustrate the preparation of the compounds of the present invention. They are not meant to be limiting in scope. Melting points are uncorrected. NMR data are reported in parts per million and are referenced to the deuterium lock signal from the sample solvent.

EXAMPLES

Example 1

(3S,5R)-3-Amino-5-methyl-octanoic acid hydrochloride (R)-2,6-Dimethyl-non-2-ene. To (S)-citronellyl bromide (50 g, 0.228 mol) in THF (800 mL) at 0° C. was added LiCl (4.3 g) followed by $CuCl_2$ (6.8 g). After 30 minutes methylmagnesium chloride (152 mL of a 3 M solution in THF, Aldrich) was added and the solution warmed to room temperature. After 10 hours the solution was cooled to 0° C. and a saturated aqueous solution of ammonium chloride carefully added. The resultant two layers were separated and the aqueous phase extracted with ether. The combined organic phases were dried ($MgSO_4$) and concentrated to give (R)-2,6-dimethyl-non-2-ene. 32.6 g; 93%. Used without further purification. $^1H$ NMR (400 MHz; $CDCl_3$) δ 5.1 (m, 1H), 1.95 (m, 2H), 1.62 (s, 3H), 1.6 (s, 3H), 1.3 (m, 4H), 1.2 (m, 2H), 0.8 (s, 6H); $^{13}C$ NMR (100 MHz; $CDCl_3$) δ 131.13, 125.28, 39.50, 37.35, 32.35, 25.92, 25.77, 20.31, 19.74, 17.81, 14.60.

(R)-4-Methyl-heptanoic acid. To (R)-2,6-dimethyl-non-2-ene (20 g, 0.13 mol) in acetone (433 mL) was added a solution of $CrO_3$ (39 g, 0.39 mol) in $H_2SO_4$ (33 mL)/$H_2O$ (146 mL) over 50 minutes. After 6 hours a further amount of $CrO_3$ (26 g, 0.26 mol) in $H_2SO_4$ (22 mL)/$H_2O$ (100 mL) was added. After 12 hours the solution was diluted with brine and the solution extracted with ether. The combined organic phases were dried ($MgSO_4$) and concentrated. Flash chromatography (gradient of 6:1 to 2:1 hexane/EtOAc) gave (R)-4-methyl-heptanoic acid as an oil. 12.1 g; 65%. MS, m/z (relative intensity): 143 [M–H, 100%]; $^1H$ NMR (400 MHz; $CDCl_3$) δ 2.35 (m, 2H), 1.6 (m, 1H), 1.4 (m, 1H), 1.3 (m, 4H), 1.1 (m, 1H), 0.85 (s, 6H).

(4R,5S)-4-Methyl-3-((R)-4-methyl-heptanoyl)-5-phenyl-oxazolidin-2-one. To (R)-4-methyl-heptanoic acid (19 g, 0.132 mol) and triethylamine (49.9 g, 0.494 mol) in THF (500 mL) at 0° C. was added trimethylacetylchloride (20 g, 0.17 mol). After 1 hour LiCl (7.1 g, 0.17 mol) was added followed by (4R,5S)-(+)-4-methyl-5-phenyl-2-oxazolidinone) 3 (30 g, 0.17 mol). The mixture was warmed to room temperature and after 16 hours the filtrate was removed by filtration and the solution concentrated under reduced pressure. Flash chromatography (7:1 hexane/EtOAc) gave (4R, 5S)-4-methyl-3-((R)-4-methyl-heptanoyl)-5-phenyl-oxazolidin-2-one as an oil. 31.5 g; 79%. $[α]_D$=+5.5 (c 1 in $CHCl_3$). MS, m/z (relative intensity): 304 [M+H, 100%]; $^1H$ NMR (400 MHz; $CDCl_3$) δ 7.4–7.2 (m, 5H), 5.6 (d, J=7.32 Hz, 1H), 4.75 (m, 1H), 2.96 (m, 1H), 2.86 (m, 1H), 1.62 (m, 1H), 1.43 (m, 1H), 1.25 (m, 4H), 1.12 (m, 1H), 0.85 (m, 9H); $^{13}C$ NMR (100 MHz; $CDCl_3$) δ 173.70, 153.23, 133.81, 133.59, 128.92, 128.88, 128.92, 128.88, 125.83, 79.12, 54.93, 39.24, 33.66, 32.32, 31.47, 27.18, 26.52, 20.25, 19.57, 14.75, 14.52.

(3S,5R)-5-Methyl-3-((4R,5S)-4-methyl-2-oxo-5-phenyl-oxazolidine-3-carbonyl)-octanoic acid tert-butyl ester. To (4R,5S)-4-methyl-3-((R)-4-methyl-heptanoyl)-5-phenyl-oxazolidin-2-one (12.1 g, 0.04 mol) in THF (200 ml) at –50° C. was added sodium bis(trimethylsilyl)amide (48 mL of a 1 M solution in THF). After 30 min t-butylbromoacetate (15.6 g, 0.08 mol) was added. The solution was stirred for 4 hours at –50° C. and then warmed to room temperature. After 16 hours a saturated aqueous solution of ammonium chloride was added and the two layers separated. The aqueous phase was extracted with ether and the combined organic phases dried ($MgSO_4$) and concentrated. Flash chromatography (9:1 hexane/EtOAc) gave (3S,5R)-5-methyl-3-((4R,5S)-4-methyl-2-oxo-5-phenyl-oxazolidine-3-carbonyl)-octanoic acid tert-butyl ester as a white solid 12 g; 72%. $[α]_D$=+30.2 (c 1 in $CHCl_3$). $^{13}C$ NMR (100 MHz; $CDCl_3$) δ 176.47, 171.24, 152.72, 133.63, 128.87, 125.86, 80.85, 78.88, 55.34, 39.98, 38.77, 38.15, 37.58, 30.60, 28.23, 20.38, 20.13, 14.50, 14.28.

(S)-2-((R)-2-Methyl-pentyl)-succinic acid 4-tert-butyl ester. To (3S,5R)-5-methyl-3-((4R,5S)-4-methyl-2-oxo-5-phenyl-oxazolidine-3-carbonyl)-octanoic acid tert-butyl ester (10.8 g, 0.025 mol) in $H_2O$ (73 mL) and THF (244 mL) at 0° C. was added a premixed solution of LiOH (51.2 mL of a 0.8 M solution) and $H_2O_2$ (14.6 mL of a 30% solution). After 4 hours a further 12.8 mL LiOH (0.8 M solution) and 3.65 mL of $H_2O_2$ (30% solution) was added. After 30 minutes sodium bisulfite (7 g), sodium sulfite (13 g), and water (60 mL) was added followed by hexane (100 mL) and ether (100 mL). The two layers were separated and the aqueous layer extracted with ether. The combined organic phases were concentrated to an oil that was dissolved in heptane (300 mL). The resultant solid was filtered off and the filtrate dried ($MgSO_4$) and concentrated to afford (S)-2-((R)-2-methyl-pentyl)-succinic acid 4-tert-butyl ester (6 g, 93%) which was used immediately without further purification. MS, m/z (relative intensity): 257 [M+H, 100%].

(3S,5R)-3-Benzyoxycarbonylamino-5-methyl-octanoic acid, tert-butyl ester. A solution of (S)-2-((R)-2-methyl-pentyl)-succinic acid 4-tert-butyl ester (6.0 g, 23.22 mmol) and triethylamine (3.64 mL, 26.19 mmol) in toluene (200 mL) was treated with diphenylphosphorylazide (5.0 mL, 23.22 mL) and stirred at room temperature for 0.5 hours. After the reaction mixture was then heated at reflux for 3 h and cooled briefly, benzyl alcohol was added (7.2 mL, 69.7 mmol) and the solution heated for another 3 h. After the reaction mixture was allowed to cool, it was diluted with ethyl ether (200 mL) and the combined organic layer was washed successively with saturated $NaHCO_3$ and brine and dried ($Na_2SO_4$). The concentrated organic component was purified by chromatography (MPLC) eluting with 8:1 hexanes:ethyl acetate to provide (3S,5R)-3-benzyoxycarbonylamino-5-methyl-octanoic acid, tert-butyl ester (6.4 g, 75.8%). MS: M+1: 364.2, 308.2. $^1$HNMR (400 MHz, $CDCl_3$) δ 0.83 (t, 3H, J=6.59 Hz), 0.87 (d, 3H, J=6.59 Hz), 1.08–1.34 (m, 6H), 1.39 (s, 9H), 1.41–1.52 (m, 2H), 2.39 (m, 2H), 4.02 (m, 1H), 5.05 (s, 2H), 5.09 (m, 1H), and 7.24–7.32 (m, 5H) ppm.

(3S,5R)-3-Amino-5-methyl-octanoic acid, tert-butyl ester. A solution of (3S,5R)-3-benzyoxycarbonylamino-5-methyl-octanoic acid, tert-butyl ester (2.14 g, 5.88 mmol) in THF (50 mL) was treated with Pd/C (0.2 g) and $H_2$ at 50 psi for 2 hours. The reaction mixture was then filtered and concentrated to an oil in vacuo to give (3S,5R)-3-amino-5-methyl-octanoic acid, tert-butyl ester in quantitative yield. MS: M+1: 230.2, 174.1. $^1$HNMR (400 MHz, $CDCl_3$) δ 0.85–0.86 (overlapping t and d, 6H), 1.13–1.40 (m, 6H), 1.44 (s, 9H), 1.60 (m, 1H), 2.31 (dd, 1H, J=7.81 and 15.86 Hz), 2.38(dd, 1H, J=5.13 and 15.86 Hz), 3.31 (m, 1H), and 3.45(br s, 2H) ppm.

(3S,5R)-3-Amino-5-methyl-octanoic acid hydrochloride. A slurry of (3S,5R)-amino-5-methyl-octanoic acid, tert-butyl ester (2.59 g, 11.3 mmol) in 6N HCl (100 mL) was heated under reflux 18 hours, cooled, and filtered over Celite. The filtrate was concentrated in vacuo to 25 mL and the resulting crystals were collected and dried to provide (3S,5R)-3-amino-5-methyl-octanoic acid hydrochloride, mp 142.5–142.7° C. (1.2 g, 50.56%). A second crop (0.91 g) was obtained from the filtrate. Anal. Calc'd for $C_9H_{19}NO_2 \cdot HCl$: C: 51.55, H: 9.61, N: 6.68, Cl: 16.91. Found: C: 51.69, H: 9.72, N: 6.56, Cl: 16.63. MS: M+1: 174.1. $^1$HNMR ($CD_3OD$) δ 0.89 (t, 3H, J=7.32 Hz), 0.92 (d, 3H, J=6.35 Hz), 1.12–1.18 (m, 1H), 1.25–1.35 (m, 2H), 1.35–1.42 (m, 2H), 1.54–1.64 (m, 2H), 2.50 (dd, 1H, J=7.81 and 17.33 Hz), 2.65 (dd, 1H, J=4.64 and 17.32 Hz), and 3.52 (m, 1H) ppm.

(3S,5R)-3-Amino-5-methyl-octanoic acid hydrochloride acid salt. 5.3 g of 2S-(2R-methyl-pentyl)-succinic acid-4-tert-butyl ester contained in 30 mL methyltertbutyl ether is reacted at room temperature with 3.5 mL triethylamine followed by 6.4 g of diphenylphosphoryl azide. After allowing the reaction to exotherm to 45° C. and stirring for at least 4 hours, the reaction mixture is allowed to cool to room temperature and stand while the phases separated. The lower layer is discarded and the upper layer is washed with water, followed by dilute aqueous HCl. The upper layer is then combined with 10 mL of 6 N aqueous HCl, and stirred at 45–65° C. The reaction mixture is concentrated by vacuum distillation to about 10–14 mL and allowed to crystallize while cooling to about 5° C. After collecting the product by filtration, the product is washed with toluene and reslurried in toluene. The product is dried by heating under vacuum resulting in 2.9 g (67%) of white crystalline product. The product may be recrystallized from aqueous HCl. mp 137° C., HNMR (400 MHz, D6 DMSO) delta 0.84–0.88 (overlapping d and t, 6H), 1.03–1.13 (m, 1H), 1.16–1.37 (m, 4H), 1.57–1.68 (m, 2H), 2.55 (dd, 1H, J=7, 17 Hz), 2.67 (dd, 1H, J=6, 17 Hz), 3.40 (m, 1H), 8.1 (br s, 3H), 12.8 (br s, 1H).

Example 2

(3S,5R)-Amino-5-methyl-heptanoic acid

Methanesulfonic acid (S)-3,7-dimethyl-oct-6-enyl ester. To S-(−)-citronellol (42.8 g, 0.274 mol) and triethylamine (91 mL, 0.657 mol) in $CH_2Cl_2$ (800 mL) at 0° C. was added methanesulphonyl chloride (26 mL, 0.329 mol) in $CH_2Cl_2$ (200 mL). After 2 hours at 0° C. the solution was washed with 1N HCl then brine. The organic phase was dried ($MgSO_4$) and concentrated to afford the titled compound an oil (60.5 g, 94%) which was used without further purification. MS, m/z (relative intensity): 139 [100%], 143 [100%]. $^1$H NMR (400 MHz; $CDCl_3$) δ 5.05 (1H, m), 4.2 (2H, m), 2.95 (3H, s), 1.98 (2H, m), 1.75 (1H, m), 1.6 (3H, s), 1.5 (4H, m), 1.35 (2H, m), 1.2 (1H, m), 0.91 (3H, d, J=6.5 Hz).

(R)-2,6-Dimethyl-oct-2-ene. To methanesulfonic acid (S)-3,7-dimethyl-oct-6-enyl ester (60 g, 0.256 mol) in THF (1 L) at 0° C. was added lithium aluminum hydride (3.8 g, 0.128 mol). After 7 hours, a further 3.8 g of lithium aluminum hydride was added and the solution warmed to room temperature. After 18 hours, a further 3.8 g of lithium aluminum hydride was added. After a further 21 hours, the reaction was carefully quenched with 1 N citric acid and the solution diluted further with brine. The resultant two phases were separated and the organic phase was dried ($MgSO_4$) and concentrated to afford the titled compound as an oil which was used without further purification. MS, m/z (relative intensity): 139 [M+H, 100%].

(R)-4-Methyl-hexanoic acid. A procedure similar to the synthesis of (R)-4-methyl-heptanoic acid was utilized giving the acid as an oil (9.3 g, 56%). IR (film) 2963, 2931, 2877, 2675, 1107, 1461, 1414 $cm^{-1}$; MS, m/z (relative intensity): 129 [M−H, 100%]; $^1$H NMR (400 MHz; $CDCl_3$) δ 2.35 (m, 2H), 1.66 (m, 1H), 1.37 (m, 4H), 1.29 (m, 1H), 0.86 (m, 6H); $^{13}$C NMR (100 MHz; $CDCl_3$) δ 181.02, 34.09, 32.12, 31.39, 29.29, 18.94, 11.44.

(4R,5S)-4-Methyl-3-((R)-4-methyl-hexanoyl)-5-phenyl-oxazolidin-2-one. A procedure similar to the synthesis of (4R,5S)-4-methyl-3-((R)-4-methyl-heptanoyl)-5-phenyl-oxazolidin-2-one was utilized giving the titled compound as an oil (35.7 g, 95%). MS, m/z (relative intensity): 290 [M+H, 100%]; $^1$H NMR (400 MHz; $CDCl_3$) δ 7.4–7.25 (m, 5H), 5.6 (d, J=7.32 Hz, 1H), 4.75 (m, 1H), 2.97 (m, 1H), 2.85 (m, 1H), 1.68 (m, 1H), 1.43 (m, 2H), 1.12 (m, 2H), 0.87 (m, 9H); $^{13}$C NMR (100 MHz; $CDCl_3$) δ 173.71, 153.24, 133.56, 128.94, 128.90, 125.83, 79.14, 54.95, 34.22, 33.72, 31.07, 29.45, 27.20, 26.52, 19.19, 19.15, 14.77, 14.53, 11.54.

(3S,5R)-5-Methyl-3-[1-((4R,5S)-4-methyl-2-oxo-5-phenyl-oxazolidin-3-yl)-methanoyl]-heptanoic acid tert-butyl ester. A procedure similar to the preparation of (3S,5R)-5-methyl-3-((4R,5S)-4-methyl-2-oxo-5-phenyl-oxazolidine-3-carbonyl)-octanoic acid tert-butyl ester was followed giving the titled compound as an oil (7.48 g; 31%). IR (film) 2967, 2934, 1770, 1716, 1696, 1344, 1148, 1121, 1068, 1037, 947 cm$^{-1}$; MS, m/z (relative intensity): 178 [100%], 169 [100%]; [α]$_D$=+21.6 (c 1 in CHCl$_3$).

(S)-2-((R)-2-Methyl-butyl)-succinic acid 4-tert-butyl ester. (3S,5R)-5-Methyl-3-[1-((4R,5S)-4-methyl-2-oxo-5-phenyl-oxazolidin-3-yl)-methanoyl]-heptanoic acid tert-butyl ester (7.26 g, 0.018 mol) in H$_2$O (53 mL) and THF (176 mL) at 0° C. was added a premixed solution of LiOH (37 mL of a 0.8 M solution) and H$_2$O$_2$ (10.57 mL of a 30% solution) and the solution warmed to room temperature. After 2 hours sodium bisulfite (7 g), sodium sulfite (13 g), and water (60 mL) was added and the two layers were separated and the aqueous layer extracted with ether. The combined organic phases were concentrated to an oil that was dissolved in heptane (200 mL). The resultant solid was filtered off and the filtrate dried (MgSO$_4$) and concentrated to afford the titled compound as an oil (4.4 g) that was used without further purification. MS, m/z (relative intensity): 243 [100%]; $^1$H NMR (400 MHz; CDCl$_3$) δ 2.88 (m, 1H), 2.59 (m, 1H), 2.36 (m, 1H), 1.65 (m, 1H), 1.41 (s, 9H), 1.20 (m, 4H), 0.84 (m, 6H)

(3S,5R)-3-Benzyoxycarbonylamino-5-methyl-heptanoic acid, tert-butyl ester—This compound was prepared as described above starting with (S)-2-((R)-2-methyl-butyl) succinic acid, 4-tert-butyl ester to give (3S,5R)-3-benzyoxycarbonylamino-5-methyl-heptanoic acid, tert-butyl ester as an oil (73.3% yield). $^1$H NMR (400 MHz; CDCl$_3$) δ 0.84(t, 3H, J=7.33 Hz), 0.89(d, 3H, J=6.60 Hz), 1.12–1.38 (m, 4H), 1.41 (s, 9H), 1.43–1.59 (m, 2H), 2.42 (m, 2H), 4.05 (m, 1H), 5.07 (t, 2H J=12.95 Hz), and 7.28–7.34 (m, 5H).

(3S,5R)-Amino-5-methyl-heptanoic acid, tert-butyl ester—This compound was prepared as described above starting with (3S,5R)-3-benzyoxycarbonylamino-5-methyl-heptanoic acid, tert-butyl ester instead of (3S,5R)-3-benzyoxycarbonylamino-5-methyl-octanoic acid, tert-butyl ester to give the titled compound. $^1$H NMR (400 MHz; CDCl$_3$) δ 0.84 (overlapping t and d, 6H), 1.08–1.16(m, 2H), 1.27–1.30 (m, 2H), 1.42(s, 9H), 1.62 (br s, 2H), 2.15 (dd, 1H, J=8.54 and 15.62 Hz), 2.29(dd, 1H, J=4.15 and 15.37 Hz), and 3.20(br s, 2H).

(3S,5R)-Amino-5-methyl-heptanoic acid hydrochloride—A slurry of (3S,5R)-amino-5-methyl-heptanoic acid, tert-butyl ester (1.44 g, 6.69 mmol) in 3N HCl was heated at reflux for 3 hours, filtered hot over Celite, and concentrated to dryness. Trituration of the resulting solid in ethyl ether provided (3S,5R)-3-amino-5-methyl-heptanoic acid hydrochloride, (0.95 g, 85%) mp 126.3–128.3° C. $^1$H NMR (400 MHz; CD$_3$OD) δ 0.92 (t, 3H, J=7.32 Hz), 0.92 (d, 3H, J=6.35 Hz), 1.15–1.24 (m, 1H), 1.33–1.43 (m, 2H), 1.44–1.52 (m, 1H), 1.60–1.67 (m, 1H), 2.57 (ddd, 1H, J=7.32 17.67 and 5.12 Hz), 2.69 (ddd, 1H, J=0.97, 4.88 and 17.32 Hz), and 3.28 (m, 1H). Anal. Calc'd for C$_8$H$_{17}$NO$_2$.HCl.0.1H$_2$O: C: 48.65, H: 9.29, N: 7.09, Cl: 17.95. Found: C: 48.61, H: 9.10, N: 7.27, Cl: 17.87MS: M+1: 160.2.

Example 3

(3S,5R)-3-Amino-5-methyl-nonanoic acid (R)-4-Methyl-octanoic acid. Lithium chloride (0.39 g, 9.12 mmol) and copper (I) chloride (0.61 g, 4.56 mmol) were combined in 45 ml THF at ambient temperature and stirred 15 minutes, then cooled to 0° C. at which time ethylmagnesium bromide (1 M solution in THF, 45 mL, 45 mmol) was added. (S)-citronellyl bromide (5.0 g, 22.8 mmol) was added dropwise and the solution was allowed to warm slowly to ambient temperature with stirring overnight. The reaction was quenched by cautious addition of sat. NH$_4$Cl (aq), and stirred with Et$_2$O and sat. NH$_4$Cl (aq) for 30 minutes. The phases were separated and the organic phase dried (MgSO$_4$) and concentrated. The crude (R)-2,6-dimethyl-dec-2-ene was used without purification. To a solution of (R)-2,6-dimethyl-dec-2-ene (3.8 g, 22.8 mmol) in 50 mL acetone at 0° C. was added Jones' reagent (2.7 M in H$_2$SO$_4$ (aq), 40 mL, 108 mmol) and the solution was allowed to warm slowly to ambient temperature with stirring overnight. The mixture was partitioned between Et$_2$O and H$_2$O, the phases were separated, and the organic phase washed with brine, dried (MgSO$_4$), and concentrated. The residue was purified by flash chromatography (8:1 hexanes: EtOAc) to afford 2.14 g (59%) of the titled compound as a colorless oil: LRMS: m/z 156.9 (M+); $^1$H NMR (400 MHz; CDCl$_3$): δ 2.33 (m, 2H), 1.66 (m, 1H), 1.43 (m, 2H), 1.23 (m, 5H), 1.10 (m, 1H), 0.86 (m, 6H). Jones' reagent was prepared as a 2.7M solution by combining 26.7 g CrO$_3$, 23 mL H$_2$SO$_4$, and diluting to 100 mL with H$_2$O.

(4R,5S)-4-Methyl-3-((R)-4-methyl-octanoyl)-5-phenyl-oxazolidin-2-one. To (R)-4-methyl-octanoic acid (2.14 g, 13.5 mmol) in 25 mL CH$_2$Cl$_2$ at 0° C. was added 3 drops DMF, followed by oxalyl chloride (1.42 mL, 16.2 mmol) resulting in vigorous gas evolution. The solution was warmed directly to ambient temperature, stirred 30 minutes, and concentrated. Meanwhile, to a solution of the oxazolidinone (2.64 g, 14.9 mmol) in 40 mL THF at −78° C. was added n-butyllithium (1.6 M soln in hexanes, 9.3 mL, 14.9 mmol) dropwise. The mixture was stirred for 10 minutes at which time the acid chloride in 10 mL THF was added dropwise. The reaction was stirred 30 minutes at −78° C., then warmed directly to ambient temperature and quenched with sat. NH$_4$Cl. The mixture was partitioned between Et$_2$O and sat. NH$_4$Cl (aq), the phases were separated, and the organic phase dried (MgSO$_4$), and concentrated to furnish 3.2 g of the titled compound as a colorless oil. LRMS: m/z 318.2 (M+); $^1$H NMR (400 MHz; CDCl$_3$): δ 7.34 (m, 5H), 5.64 (d, J=7.3 Hz, 1H), 4.73 (quint, J=6.8 Hz, 1H), 2.96 (m, 1H), 2.86 (m, 1H), 1.66 (m, 1H), 1.47 (m, 2H), 1.26 (m, 5H), 1.13 (m, 1H), 0.88 (m, 9H). The crude product was used without purification.

(3S,5R)-5-Methyl-3-((4R,5S)-4-methyl-2-oxo-5-phenyl-oxazolidine-3-carbonyl)-nonanoic acid tert-butyl ester. To a solution of diisopropylamine (1.8 mL, 12.6 mmol) in 30 mL THF at −78° C. was added n-butyllithium (1.6 M soln in hexanes, 7.6 mL, 12.1 mmol), and the mixture stirred 10 minutes at which time (4R,5S)-4-Methyl-3-((R)-4-methyl-octanoyl)-5-phenyl-oxazolidin-2-one (3.2 g, 10.1 mmol) in 10 mL THF was added dropwise. The solution was stirred for 30 minutes, t-butyl bromoacetate (1.8 mL, 12.1 mmol) was added quickly dropwise at −50° C., and the mixture was allowed to warm slowly to 10° C. over 3 hours. The mixture was partitioned between Et$_2$O and sat. NH$_4$Cl (aq), the phases were separated, and the organic phase dried (MgSO$_4$), and concentrated. The residue was purified by flash chromatography (16:1 to 8:1 hexanes:EtOAc) to provide 2.65 g (61%) of the titled compound as a colorless crystalline solid, mp=84–86° C. [α]$_D^{23}$ +17.1 (c=1.00, CHCl$_3$); $^1$H NMR (400 MHz; CDCl$_3$): δ 7.34 (m, 5H), 5.62 (d, J=7.3 Hz, 1H), 4.73 (quint, J=6.8 Hz, 1H), 4.29 (m, 1H), 2.67 (dd, J=9.8, 16.4 Hz, 1H), 2.40 (dd, J=5.1, 16.4 Hz, 1H), 1.69 (m, 1H), 1.38 (s, 9H), 1.28 (m, 7H), 1.08 (m, 1H), 0.88 (m, 9H); $^{13}$C NMR (400 MHz; CDCl$_3$) δ 176.45, 171.22, 152.71, 133.64, 128.86, 125.86, 80.83, 78.87, 55.33, 40.02, 38.21, 37.59, 36.31, 30.86, 29.29, 28.22, 23.14, 20.41, 14.36, 14.26. Anal. Calcd for C$_{25}$H$_{37}$NO$_5$: C, 69.58; H, 8.64; N, 3.25. Found: C, 69.37; H, 8.68; N, 3.05.

(S)-2-((R)-2-Methyl-hexyl)-succinic acid 4-tert-butyl ester. To a solution of (3S,5R)-5-Methyl-3-((4R,5S)-4-methyl-2-oxo-5-phenyl-oxazolidine-3-carbonyl)-nonanoic acid tert-butyl ester (2.65 g, 6.14 mmol) in 20 mL THF at 0° C. was added a precooled (0° C.) solution of LiOH monohydrate (1.0 g, 23.8 mmol) and hydrogen peroxide (30 wt % aqueous soln, 5.0 mL) in 10 mL H$_2$O. The mixture was stirred vigorously for 90 minutes, then warmed to ambient temperature and stirred 90 minutes. The reaction was quenched at 0° C. by addition of 100 mL 10% NaHSO$_3$ (aq), then extracted with Et$_2$O. The phases were separated, and the organic phase washed with brine, dried (MgSO$_4$), and concentrated. The titled compound was used without purification.

(3S,5R)-3-Benzyoxycarbonylamino-5-methylnonanoic acid, tert-butyl ester-This compound was prepared similarly as described above starting with (S)-2-((R)-2-methylhexyl) succinic acid, 4-tert-butyl ester instead of (S)-2-((R)-2-methylpentyl) succinic acid, 4-tert-butyl ester to provide the titled compound as an oil (71.6% yield). $^1$HNMR (400 MHz; CDCl$_3$) δ 0.81(t, 3H, J=4.40 Hz), 0.85(d, 3H, J=6.55 Hz), 1.06–1.20(m, 7H), 1.36(s, 9H), 1.38–1.50(m, 2H), 2.36(m, 2H), 3.99(m, 1H), 5.02(m+s, 3H), and 7.28–7.28(m, 5H).

(3S,5R)-3-Amino-5-methyl-nonanoic acid, tert-butyl ester—This compound was prepared as described above starting with (3S,5R)-benzyoxycarbonylamino-5-methyl-nonanoic acid, tert-butyl ester instead of (3S,5R)-3-benzyoxycarbonylamino-5-methyl-octanoic acid, tert-butyl ester. Yield=97%. $^1$HNMR (400 MHz; CDCl$_3$) δ 0.82(overlapping d and t, 6H), 1.02–1.08(m, 1H), 1.09–1.36(m, 6H), 1.39(s, 9H), 1.47(br s, 1H), 1.80(s, 2H), 2.13(dd, 1H, J=8.54 and 15.61 Hz), and 2.27(dd, 1H, J=4.15 and 15.38 Hz).

(3S,5R)-3-Amino-5-methyl-nonanoic acid hydrochloride—A mixture of (3S,5R)-3-amino-5-methyl-nonanoic acid, tert-butyl ester (1.50 g, 6.16 mmol) in 3N HCl (100 mL) was heated at reflux for 3 hours, filtered hot over Celite, and concentrated to 30 mL in vacuo. The resulting crystals were collected, washed with additional 3N HCl, and dried to provide the title compound, mp 142.5–143.3° C. Additional crops were obtained from the filtrate to provide 1.03 g (70.4%). $^1$HNMR (400 MHz; CD$_3$OD) δ=0.91(t, 3H, J=6.84 Hz), 0.92(d, 3H, J=6.35 Hz), 1.16–1.26(m, 1H), 1.27–1.35 (m, 4H), 1.38–1.45(m, 1H), 1.61 (br s, 1H), 1.63–1.68(m, 1H), 2.58 (dd, 1H, J=7.32 and 17.34 Hz), 2.69(dd, 1H, J=5.13 and 17.59 Hz), and 3.59(m, 1H). Anal. Calc'd for C$_{10}$H$_{21}$NO$_2$.HCl: C: 53.68, H: 9.91, N: 6.26, Cl: 15.85. Found: C: 53.89, H: 10.11, N: 6.13. MS: M+1: 188.1.

Example 4

(2R,4R)-2-Aminomethyl-4-methyl-heptanoic acid

5R-Methyl-3R-(4S-methyl-2-oxo-5R-phenyloxazolidine-3-carbonyl)octanoic acid. A solution of (3R,5R)-5-Methyl-3-((4S,5R)-4-methyl-2-oxo-5-phenyl-oxazolidine-3-carbonyl)-octanoic acid tert-butyl ester(3.9 g, 9.34 mmol) in dichloromethane (150 mL) was treated with trifluoroacetic acid (7.21 mL, 93.4 mL) and stirred 18 hours at ambient temperature. After the solvents and reagent were removed in vacuo, the resulting residue was triturated in 100 mL hexanes to provide 3.38 g of the title compound (100%) mp 142–143° C. MS M+1=362.1. $^1$H NMR (400 MHz; CDCl$_3$) δ 0.85(2t, 6H, J=7.1 Hz), 0.93(d, 3H, J=6.1 Hz), 1.14(m, 1H), 1.2–1.49(m, 6H), 2.56(dd, 1H, J=4.15 and 17.57 Hz), 2.81(dd, 1H, J=17.33 and 10.74 Hz), 4.28(m, 1H), 4.74 (quint, 1H, J=6.84 Hz), 5.64(d, 1H, J=7.32 Hz), 7.29–7.43 (m, 5H).

[4R-Methyl-2R-(4S-methyl-2-oxo-5R-phenyloxazolidine-3-carbonyl)heptyl]carbamic acid benzyl ester. A solution of 5R-methyl-3R-(4S-methyl-2-oxo-5R-phenyloxazolidine-3-carbonyl)octanoic acid (1.98 g, 5.48 mmol) and triethylamine (0.92 mL, 6.57 mmol) was treated with diphenylphosphorylazide (1.2 mL, 5.48 mmol), stirred 30 min at ambient temperature and then heated at reflux for 3 hours. After cooling briefly, the reaction mixture was treated with benzyl alcohol (2.8 mL, 27.4 mmol) and heated for an additional 3 h at reflux. The reaction mixture was cooled, diluted with ethyl ether (150 mL), washed successively with sat'd NaHCO$_3$ and brine, dried (MgSO$_4$) and concentrated in vacuo to an oil. Chromatography (MPLC, elution with 4:1 hexanes:ethyl acetate) provided the title compound (2.0 g, 78.3%) as an oil. MS M+1=467.1. $^1$H NMR (400 MHz; CDCl$_3$) δ 0.86(2t, 6H, J=7.1 Hz), 0.93(d, 3H, J=5.9 Hz), 1.14(m, 1H), 1.09–1.36(m, 6H), 1.50(d, 1H, J=5.2 Hz), 3.49(t, 1H, J=6.1 Hz), 4.10(m, 1H), 4.71 (quint, 1H, J=6.61 Hz), 5.06(d, 2H, J=3.42 Hz), 5.20(t, 1H, J=5.61 Hz), 5.64(d, 1H, J=7.08 Hz), 7.29–7.43(m, 10H).

2R-(Benzyloxycarbonylaminomethyl)-4R-methylheptanoic acid. A solution of 4R-methyl-2R-(4S-methyl-2-oxo-5R-phenyloxazolidine-3-carbonyl)heptyl]carbamic acid benzyl ester (4.12 g, 8.83 mmol) in 3:1 THF:water (100 mL) was cooled to 0° C. and treated with a mixture of 0.8 N LiOH (17.5 mL, 14 mmol) and 30% H$_2$O$_2$ (4.94 mL, 44 mmol). After the reaction mixture was stirred in the cold 3 hours, it was quenched with a slurry of NaHSO$_3$ (2.37 g) and Na$_2$SO$_3$ (4.53 g) in water (30 mL) and stirred 1 hour. The reaction mixture was diluted with ethyl ether (200 mL), partitioned, and the organic layer washed with brine and dried (MgSO$_4$). The concentrated organic extract was chromatographed (MPLC) eluting with ethyl acetate to give 1.25 g of 2R-(benzyloxycarbonylaminomethyl)-4R-methylheptanoic acid (46%). MS M+1=308.1. $^1$H NMR (400 MHz; CDCl$_3$) δ 0.83(t, 3H, J=6.84 Hz), 0.87(t, 3H, J=6.35 Hz), 1.14(m, 1H), 1.06–1.54(m, 7H), 2.7(br s, 1H), 3.30(m, 2H), 5.05(q, 2H, J=12.2 Hz), 5.14(t, 1H, J=5.61 Hz), 7.30(br s, 5H).

(2R,4R)-2-Amino-4-methyl-heptanoic acid hydrochloride. A mixture of 2R-(benzyloxycarbonylaminomethyl)-4-methyl-heptanoic acid (1.25 g, 4.07 mmol) and Pd/C (20%, 0.11 g) in methanol (50 mL) was hydrogenated at 50 psi for 18 hours. After the catalyst was removed by filtration, the solvent was removed in vacuo and the resulting solid triturated in ether to provide (2S,4R)-2-amino-4-methyl-heptanoic acid hydrochloride (0.28 g, 40%) mp 226.3–228.0° C. MS M+1=174.0. $^1$H NMR (400 MHz; CD$_3$OD) δ 0.89(t+d, 6H, J=6.35 Hz), 1.11 (m, 1H), 1.25–1.40(m, 4H), 1.47–1.62(m, 2H), 2.48(br s, 1H), 2.93 (m, 2H). Anal. Calc'd for C$_9$H$_{19}$NO$_2$.0.1H$_2$OC: 61.75H: 11.06 N: 8.00. Found C: 61.85; H: 10.83; N: 8.01.

Example 5

2-Aminomethyl-4,4-dimethyl-heptanoic acid hydrochloride

2-Cyano-4,4-dimethyl-hepta-2,6-dienoic acid ethyl ester. A solution of 2,2-dimethyl-pent-4-enal (5.0 g, 44 mmol), cyano-acetic acid ethyl ester (5.12 mL, 48 mmol), piperidine (1.3 mL, 14 mmol) and acetic acid (4.52 mL, 80 mmol) in 170 mL of toluene was heated under reflux for 18 hours in a flask equipped with a Dean-Stark separator. Several mL of water was collected in the trap. The reaction was cooled and washed with 1N HCl, $NaHCO_3$ and brine, successively. The organic layers were dried over $Na_2SO_4$ and concentrated to an oil. This oil was chromatographed eluting with 20% of EtOAc in hexane to give a combination of two lots total 8.3 g (91%). $^1H$ NMR (400 MHz; $CDCl_3$) 1.28 (s, 6H), 1.32 (t, 3H, J=7 Hz), 2.26 (d, 2H, J=7.6 Hz), 4.27 (q, 2H, J=7.2 Hz), 5.08 (d, 1H, J=12 Hz), 5.10 (d, 1H, J=4 Hz), 5.72 (m, 1H).

2-Aminomethyl-4,4-dimethyl-heptanoic acid hydrochloride. 2-Cyano-4,4-dimethyl-hepta-2,6-dienoic acid ethyl ester (5.88 g, 28 mmol) was dissolved in the mixture of 91 mL of ethanol and 6 mL of HCl and treated with 0.4 g of $PtO_2$. The reaction was carried out under 100 psi of hydrogen pressure at room temperature for 15 hours. The catalyst was filtered and filtrate was concentrated to give 3.8 g of the desired product 2-aminomethyl-4,4-dimethyl-heptanoic acid ethyl ester as an oil. MS (APCI): 216.2 $(M+1)^+$. This oil was refluxed in 75 mL of 6N HCl for 18 hours. While the reaction was cooled, a precipitate formed. The solid was filtered, washed with additional HCl solution and triturated with ether to give the clean title compound. MS (APCI): 188.1 $(M+1)^+$. 186.1 $(M-1)^+$. $^1H$ NMR (400 MHz; $CD_3OD$): 0.91 (9H, m), 1.30 (5H, m), 1.81 (dd, 1H, J=7.2 Hz, 14.4 Hz), 2.72 (1H, m), 3.04 (2H, m); Anal. Calc'd for $C_{10}H_{21}NO_2.HCl$: C: 53.68, H: 9.91, N: 6.26, Cl: 15.85; Found: C: 53.83, H: 10.15, N: 6.22, Cl: 15.40. MP: 229.5–231.0° C.

Example 6

(S)-3-Amino-5,5-dimethyl-octanoic acid 3-(4,4-Dimethyl-heptanoyl)-(R)-4-methyl-(S)-5-phenyl-oxazolidin-2-one: A solution of 4,4-dimethyl-heptanoic acid (1.58 g, 10 mmol) and triethylamine (4.6 mL) in 50 mL THF was cooled to 0° C. and treated with 2,2-dimethyl-propionyl chloride (1.36 mL). After one hour, 4R-methyl-5S-phenyl-oxazolidin-2-one (1.95 g, 11 mmol) and lithium chloride (0.47 g, 11 mmol) was added and the mixture was stirred for 18 hours. The precipitate was filtered and washed thoroughly with additional THF. The filtrate was concentrated in vacuo to give an oily solid. This solid was dissolved in 200 mL $Et_2O$, washed successively with saturated $NaHCO_3$, 0.5N HCl and saturated NaCl, dried ($MgSO_4$) and concentrated in vacuo to give the title compound as an oil (3.0 g, 95%). $^1HNMR$ (400 MHz; $CDCl_3$): 0.73–0.84 (m, 12H), 1.10–1.22 (m, 4H), 1.46–1.54 (m, 2H), 2.75–2.87 (m, 2H), 4.70 (m, 1H, J=7 Hz), 5.59 (d, 1H, J=7 Hz), 7.22–7.37 (m, 5H).

5,5-Dimethyl-(S)-3-((R)-4-methyl-2-oxo-(S)-5-phenyl-oxazolidine-3-carbonyl)-octanoic acid tert-butyl ester: According to example 1, 5.07 g (16 mmol) of 3-(4,4-dimethyl-heptanoyl)-4-methyl-5-phenyl-oxazolidin-2-one, 18 mL (1N, 18 mmol) of NaHMDS solution and 4.72 mL (32 mmol) of bromo-acetic acid tert-butyl ester gave 3.40 g (49.3%) of the title compound as a crystalline solid. $^1HNMR$ (400 MHz; $CDCl_3$): 0.85–0.89 (m, 12H), 1.18–1.32 (m, 6H), 1.41 (s, 9H), 1.88 (dd, 1H, J=6 Hz, 8.4 Hz), 2.41 (dd, 1H, J=6 Hz, 16 Hz), 2.62 (dd, 1H, J=8.4 Hz, 16 Hz), 4.30–4.40 (m, 1H), 4.72 (m, 1H), 5.62 (d, 1H, J=7 Hz), 7.30–7.40 (m, 5H). m.p.: 83–85° C.

(S)-2-(2,2-Dimethyl-pentyl)-succinic acid 4-tert-butyl ester: According to example 1, 3.4 g (7.9 mmol) of 5,5-dimethyl-3-(4-methyl-2-oxo-5-phenyl-oxazolidine-3-carbonyl)-octanoic acid tert-butyl ester, 16 mL (12.8 mmol) of 0.8N LiOH and 4.5 mL of 30% $H_2O_2$ gave 2.42 g (>100%) of the title compound as an oil. $^1HNMR$ (400 MHz; $CDCl_3$): 0.77–0.82 (m, 9H), 1.14–1.29 (m, 5H), 1.42 (s, 9H), 1.77 (dd, 1H, J=8 Hz, 16 Hz), 2.36 (dd, 1H, J=6 Hz, 16 Hz), 2.59 (dd, 1H, J=8 Hz, 16 Hz), 2.75–2.85 (m, 1H).

(S)-3-Benzyloxycarbonylamino-5,5-dimethyl-octanoic acid tert-butyl ester: According to example 1, 2.14 g (7.9 mmol) of 2-(2,2-dimethyl-pentyl)-succinic acid 4-tert-butyl ester, 1.7 mL of DPPA, 1.1 mL of $Et_3N$ and 2.44 mL of BnOH provided 1.63 g (54.8% in two steps) of the title compound as an oil. $^1HNMR$ (400 MHz; $CDCl_3$): 0.78–0.89 (m, 9H), 1.10–1.30 (m, 5H), 1.36 (s, 9H), 2.39 (t, 2H, J=5 Hz), 4.95–4.05 (m, 1H), 5.00 (s, 2H), 5.09 (d, 1H, J=9.6 Hz), 7.22–7.30 (m, 5H).

(S)-3-Amino-5,5-dimethyl-octanoic acid tert-butyl ester: According to example 1, 1.63 g of 3-benzyloxycarbonylamino-5,5-dimethyl-octanoic acid tert-butyl ester and 0.2 g of 20% Pd/C furnished the title compound. $^1HNMR$ (400 MHz; $CDCl_3$): 0.84–0.89 (m, 9H), 1.13–1.39 (m, 6H), 1.43 (s, 9H), 2.25 (dd, 1H, J=8.4 Hz, 15.6 Hz), 2.35 (dd, 1H, J=4.4 Hz, 15.6 Hz), 2.79 (s, br, 2H), 3.25–3.35 (m, 1H). MS, m/z, 244.2 $(M+1)^+$.

(S)-3-Amino-5,5-dimethyl-octanoic acid hydrochloride: According to example 1, 3-amino-5,5-dimethyl-octanoic acid tert-butyl ester was treated with 3N HCl to provide 286 mg of the title compound as a solid. $^1HNMR$ (400 MHz; $CD_3OD$): 0.87–0.93 (m, 9H), 1.18–1.31 (m, 4H), 1.51 (dd, 1H, J=4 Hz, 14.4 Hz), 1.62 (dd, 1H, J=6.8 Hz, 14.4 Hz), 2.60 (dd, 1H, J=8 Hz, 17.6 Hz), 2.73 (dd, 1H, J=4 Hz, 7.6 Hz), 3.55–3.60 (m, 1H). MS (APCI), m/z: 188.1 $(M+1)^+$. 186.1 $(M-1)^+$. Anal. Calc'd for $C_{10}H_{21}NO_2.HCl.0.12H_2O$: C: 53.17, H: 9.92, N: 6.20, Cl: 15.69; Found: C: 53.19, H: 10.00, N: 6.08, Cl: 15.25. $\alpha=+20°$ (MeOH). MP: 194.2–195.2° C.

Example 7

2-Aminomethyl-3-(1-methyl-cyclopropyl)-propionic acid

2-Cyano-3-(1-methyl-cyclopropyl)-acrylic acid ethyl ester. To 1-methylcyclopropane-methanol (Aldrich, 1.13 mL, 11.6 mmol) in 50 mL $CH_2Cl_2$ was added neutral alumina (2.5 g) and then PCC (2.5 g, 11.6 mmol), and the mixture stirred 3 h at ambient temperature. The mixture was filtered through a 1 cm plug of silica gel under vacuum, and rinsed with $Et_2O$. The filtrate was concentrated to ca. 5 mL total volume. To the residue was added THF (10 mL), ethyl cyanoacetate (1.2 mL, 11.3 mmol), piperidine (5 drops), and finally acetic acid (5 drops). The whole was stirred at ambient temperature overnight, then partitioned between $Et_2O$ and sat. aq. $NaHCO_3$. The phases were separated and the organic phase washed with brine, dried ($MgSO_4$), and concentrated. Flash chromatography of the residue (10→15% EtOAc/hexanes) provided 0.53 g (25%) of the ester as a colorless oil that crystallized on standing, mp 35–37° C. $^1H$ NMR ($CDCl_3$) δ 6.99 (s, 1H), 4.27 (q, J=7.3 Hz, 2H), 1.55 (s, 3H), 1.32 (t, J=7.3 Hz, 3H), 1.14 (s, 2H), 1.07 (s, 2H). $^{13}$C NMR δ. 170.44, 162.90, 115.17, 103.69, 62.52, 21.24, 21.07 (2C), 20.71, 14.35. Anal. Calcd for $C_{10}H_{13}NO_2$: C, 67.02; H, 7.31; N, 7.82. Found: C, 66.86; H, 7.47; N, 7.70.

2-Aminomethyl-3-(1-methyl-cyclopropyl)-propionic acid ethyl ester. To 2-cyano-3-(1-methyl-cyclopropyl)-acrylic acid ethyl ester (0.45 g, 2.51 mmol) in 16 mL EtOH:THF (1:1) was added RaNi (0.4 g), and the mixture was hydrogenated in a Parr shaker at 48 psi for 15.5 h. Pearlman's catalyst (0.5 g) was then added and hydrogenation was continued for an additional 15 h. The mixture was filtered and concentrated. Flash chromatography of the residue 2→3→4→5→6→8% MeOH/$CH_2Cl_2$ provided 0.25 g (54%) of the aminoester as a colorless oil. $^1$H NMR ($CDCl_3$) δ 3.97 (m, 2H), 2.67 (m, 2H), 2.46 (m, 1H), 1.28 (d, J=7.3 Hz, 2H), 1.19 (bs, 2H), 1.09 (t, J=7.3 Hz, 3H), 0.85 (s, 3H), 0.04 (m, 4H). LRMS: m/z 186.1 (M+1).

2-Aminomethyl-3-(1-methyl-cyclopropyl)-propionic acid. To a solution of 2-aminomethyl-3-(1-methyl-cyclopropyl)-propionic acid ethyl ester (0.25 g, 1.35 mmol) in 10 mL methanol at 0° C. was added 10% aq. NaOH (10 mL). The mixture was stirred at ambient temperature overnight, then concentrated to remove the methanol. The residue was cooled to 0° C. and acidified to pH 2 with conc. HCl. After allowing to warm to ambient temperature the mixture was loaded onto DOWEX-50WX8-100 ion exchange resin and eluted with $H_2O$ until neutral to litmus. Elution was continued with 5% aq. $NH_4OH$ (100 mL) and the alkaline fractions concentrated to provide 0.15 g (71%) of the amino acid as a colorless solid. $^1$H NMR ($CDCl_3$) δ 2.72 (m, 2H), 2.42 (m, 1H), 1.34 (dd, J=8.5, 13.9 Hz, 1H), 1.19 (dd, J=6.1, 13.9 Hz, 1H), 0.82 (s, 3H), 0.05 (m, 4H). LRMS: m/z 158.0 (M+1).

Example 8

(3S,5R)-3-Amino-5-methyl-octanoic acid (5S)-5-Methyl-octa-2,6-dienoic acid tert-butyl ester. To a solution of (S)-3-methyl-hex-4-enoic acid ethyl ester* (1.0 g, 6.4 mmol) in 30 mL toluene at −78° C. was added DIBAH (1.0M in THF, 6.4 mL) dropwise over 5 min. The mixture was stirred at −78° C. 45 min at which time 5 drops of methanol were added, resulting in vigorous $H_2$ evolution. Methanol was added until no more gas evolution was observed (ca. 5 mL). At this time the cold bath was removed and ca. 5 mL of sat. aq. $Na^+K^+$ tartrate was added. When the mixture reached room temperature, additional sat. aq. $Na^+K^+$ tartrate and $Et_2O$ were added and stirring was continued until the phases were mostly clear (ca. 1 h). The phases were separated, and the organic phase washed with brine, dried ($MgSO_4$), and concentrated to ca. 10 mL total volume owing to volatility concerns. The crude mixture was combined with an additional batch of aldehyde prepared from 10 mmol of the ester by the method described above and the whole used without purification. To a suspension of sodium hydride (60% dispersion in mineral oil) in 25 mL THF was added t-butyl-P,P-dimethylphosphonoacetate (3.0 mL, 15 mmol) dropwise over 1 h such that the evolution of $H_2$ was under control. After the addition was complete, the crude aldehyde in toluene (ca. 20 mL total volume) was added quickly dropwise and the mixture stirred at ambient temperature overnight. The mixture was partitioned between $Et_2O$ and sat. aq. $NH_4Cl$, the phases separated, the organic phase washed with brine, dried ($MgSO_4$), and concentrated. Flash chromatography of the residue (0→3→5% EtOAc/hexanes) afforded 1.0 g (29%, two steps) of the unsaturated ester as a pale yellow oil: $^1$H NMR ($CDCl_3$) δ 6.75 (m, 1H), 5.66 (m, 1H), 5.30 (m, 2H), 2.03–2.29 (m, 3H), 1.58 (d, J=6.1 Hz, 3H), 1.41 (s, 9H), 0.91 (d, J=6.6 Hz, 3H).

*(S)-3-methyl-hex-4-enoic acid ethyl ester was prepared from (S)-trans-3-Penten-2-ol [Liang, J.; Hoard, D. W.; Van Khau, V.; Martinelli, M. J.; Moher, E. D.; Moore, R. E.; Tius, M. A. *J. Org. Chem.*, 1999, 64, 1459] via Johnson-Claisen rearrangement with triethylorthoacetate according to the literature protocol [Hill, R. K.; Soman, R.; Sawada, S., *J. Org. Chem.*, 1972, 37, 3737].

(3R,5S)-3-[Benzyl-(1-phenyl-ethyl)-amino]-5-methyl-oct-6-enoic acid tert-butyl ester. To a solution of (S)-(−)-N-benzyl-α-methylbenzylamine (0.60 mL, 2.85 mmol) in 9.0 mL THF at −78° C. was added n-butyllithium (1.6M in hexanes, 1.6 mL) quickly dropwise resulting in a deep pink color. The mixture was stirred at −78° C. for 30 min at which time (5S)-5-Methyl-octa-2,6-dienoic acid tert-butyl ester (0.5 g, 2.38 mmol) in 1.0 mL THF was added slowly dropwise, resulting in a pale tan color which darkened over 3 h. The mixture was stirred 3 h at −78° C., then quenched with sat. aq. $NH_4Cl$. The mixture was allowed to warm to rt and stirred overnight, then partitioned between EtOAc and sat. aq. $NH_4Cl$. The phases were concentrated, and the organic phase dried ($MgSO_4$), and concentrated. Flash chromatography of the residue (3→5% EtOAc/hexanes) provided 0.52 g (52%) of the aminoester as a yellow oil. $^1$H NMR ($CDCl_3$) δ 7.34 (m, 2H), 7.20 (m, 8H), 5.27 (m, 2H), 3.74 (m, 1H), 3.72 (d, J=15.9 Hz, 1H), 3.41 (d, J=14.9 Hz, 1H), 3.27 (m, 1H), 2.38 (m, 1H), 1.98 (dd, J=3.7, 14.2 Hz, 1H), 1.81 (dd, J=9.3, 14.4 Hz, 1H), 1.54 (d, J=4.9 Hz, 3H), 1.32 (s, 9H), 1.24 (d, J=7.1 Hz, 3H), 0.99 (m, 2H), 0.74 (d, J=6.6 Hz, 3H).

(3S,5R)-3-Amino-5-methyl-octanoic acid. To a solution of (3R,5S)-3-[Benzyl-(1-phenyl-ethyl)-amino]-5-methyl-oct-6-enoic acid tert-butyl ester (0.92 g, 2.18 mmol) in 50 mL MeOH was added 20% Pd/C (0.20 g), and the mixture was hydrogenated in a Parr shaker at 48 psi for 23 h. The mixture was filtered and concentrated. To the crude aminoester in 10 mL $CH_2Cl_2$ was added 1.0 mL trifluoroacetic acid, and the solution stirred at ambient temperature overnight. The mixture was concentrated, and the residue dissolved in the minimum amount of $H_2O$, and loaded onto DOWEX-50WX8-100 ion exchange resin. The column was eluted with $H_2O$ until neutral to litmus, then continued with 5% aq. $NH_4OH$ (100 mL). The alkaline fractions were concentrated to provide 0.25 g (66%, two steps) of the amino acid as an off-white solid. $^1$H NMR ($CD_3OD$) δ 3.41 (m, 1H), 2.36 (dd, J=5.1, 16.6 Hz, 1H), 2.25 (dd, J=8.1, 16.6 Hz, 1H), 1.42 (m, 2H), 1.24 (m, 1H), 1.12 (m, 2H), 1.00 (m, 1H), 0.73 (d, J=6.4 Hz, 3H), 0.68 (t, J=6.8 Hz, 3H). LRMS: m/z 172.1 (M−1).

Example 9

2-Aminomethyl-8-methyl-nonanoic acid

A procedure similar to that of 2-Aminomethyl-4,4,8-trimethyl-nonanoic acid was utilized to prepare 2-Aminomethyl-8-methyl-nonanoic acid from 6-methyl-1-heptanol m/z 202.1 (M+).

2-Aminomethyl-4,8-dimethyl-nonanoic Acid (R)-2,6-dimethyl heptan-1-ol: Magnesium turnings (2.04 g, 84 mmol) and a crystal of iodine were suspended in 5 mL THF for the addition of 1-bromo-3-methyl butane (0.3 mL, neat). The mixture was heated to start the Grignard formation. The remaining 1-bromo-3-methyl butane (8.63 mL, 72 mmol) was diluted in THF (60 mL) and added dropwise. The mixture was stirred at ambient temperature for 2 hours and cooled to −5° C. A solution of copper chloride (1.21 g, 9 mmol) and LiCl (0.76 g, 18 mmol) in THF (50 mL) was added dropwise keeping the temperature below 0° C. The resulting mixture was stirred for 20 min, and (R)-3-bromo-2-methylpropanol in THF (20 mL) was added dropwise while keeping the temperature below 0° C. The mixture was allowed to slowly reach ambient temperature overnight. The reaction mixture was quenched with ammonium hydroxide and water. The mixture was diluted with EtOAc and extracted with 3×20 mL EtOAc. The organics were washed with brine, dried (MgSO₄), filtered and concentrated. The residual oil was purified via silica gel chromatography (90/10 Hexane/EtOAc) to give 2.67 g (R)-2,6-dimethyl heptan-1-ol.

(R)-1-iodo-2,6-dimethyl heptane: To a mixture of supported triphenyl phosphine (6.55 g, 19.67 mmol) in $CH_2Cl_2$ at 0° C. was added iodine (4.99 g, 19.67 mmol) and imidazole (1.33 g, 19.67 mmol). The mixture was warmed to ambient temperature, stirred for 1 h and cooled to 0° C. for the dropwise addition of (R)-2,6-dimethyl heptan-1-ol in $CH_2Cl_2$ (5 mL). The mixture was allowed to reach ambient temperature and stirred for 1 h, at which time it was filtered through a pad of celite and the solids were washed with $CH_2Cl_2$. The filtrated was concentrated, and the crude product was purified via silica gel chromatography to give (R)-1-iodo-2,6-dimethyl heptane (2.44 g).

(4R)-4,8-dimethyl nonanoic acid t-butyl ester: To diisopropyl amine (0.827 mL, 5.9 mmol) in THF (8 mL) at −78° C. was added nBuLi (2.65 mL of a 2.6 M solution in pentane). The solution was stirred for 30 min at −78° C., followed by the addition of t-butyl acetate (0.8 mL, 5.9 mmol). The mixture was stirred at −78° C. for 2 h, and then (R)-1-iodo-2,6-dimethyl heptane (0.3 g, 1.18 mmol) and HMPA (1.5 mL) in THF (1 mL) was added. The reaction was stirred at −78° C. and allowed to slowly reach ambient temperature overnight, then heated at 35° C. to drive the reaction to completion. The reaction was quenched by the addition of ammonium chloride (saturated aqueous solution), and the mixture was extracted with EtOAc (2×10 mL). The organics were combined, washed with water, dried (MgSO₄), filtered and concentrated. Silica gel chromatography (98/2 hexane/EtOAc) provided 0.25 g of (4R)-4,8-dimethyl nonanoic acid t-butyl ester.

(4R)-4,8-dimethyl nonanoic acid: (4R)-4,8-dimethyl nonanoic acid t-butyl ester in 25 mL $CH_2Cl_2$ at 0° C. was treated with TFA (6 mL). The mixture was allowed to reach ambient temperature and stir overnight. The solvent was removed by rotary evaporation, and the mixture was purified by silica gel chromatography (95/5 hexane/EtOAc) to give 0.962 g (4R)-4,8-dimethyl nonanoic acid. m/z 185 (M−).

3-(4R,8-Dimethyl-nonanoyl)-4(S)-methyl-5(R)-phenyl-oxazolidin-2-one: A procedure similar to (4R,5S)-4-Methyl-3-(R)-4-methyl-heptanoyl)-5-oxazolidin-2-one was utilized to give 3-(4R,8-Dimethyl-nonanoyl)-4(S)-methyl-5(R)-phenyl-oxazolidin-2-one (1.35 g) m/z 346.5 (M+).

[4R,8-Dimethyl-2R-(4R-methyl-2-oxo-5R-phenyl-oxazolidine-3-carbonyl)-nonyl]-carbamic acid benzyl ester: To a solution of 3-(4(R),8-Dimethyl-nonanoyl)-4(S)-methyl-5 (R)-phenyl-oxazolidin-2-one (1.05 g, 3.04 mmol) in $CH_2Cl_2$ (12 mL) and TiCl₄ (3.04 mL of a 1 M solution in $CH_2Cl_2$) was added diisopropyl ethyl amine (0.55 mL, 3.19 mmol) at −20° C. The resulting dark red solution was stirred at −20° C. for 30 min prior to the addition of a solution of N-methoxymethyl benzyl carbamate (0.652 g, 3.34 mmol) in $CH_2Cl_2$ (3.5 mL) and TiCl₄ (3.34 mL). The mixture was stirred at 0° C. for 4 h. The reaction was quenched by the addition of saturated aqueous ammonium chloride solution. The mixture was extracted with $CH_2Cl_2$ (3×15 mL). The organics were combined and washed with 1 N HCl and neutralized with NaOH, followed by washing with brine. The organics were dried (MgSO₄), filtered, concentrated and purified by silica gel chromatography (95/5 hexane/EtOAc) to give 0.555 g [4R,8-Dimethyl-2R-(4R-methyl-2-oxo-5R-phenyl-oxazolidine-3-carbonyl)-nonyl]-carbamic acid benzyl ester.

2(R)-(Benzyloxycarbonylamino-methyl)-4(R),8-dimethyl-nonanoic acid: A procedure similar to that of (S)-2-((R)-2-Methyl=pentyl)succinic acid t-butyl ester was utilized to provide 0.198 g 2(R)-(Benzyloxycarbonylamino-methyl)-4(R),8-dimethyl-nonanoic acid.

2-aminomethyl-4,8-dimethyl nonanoic acid: 2(R)-(Benzyloxycarbonylamino-methyl)-4(R),8-dimethyl-nonanoic acid (0.148 g, 0.566 mmol) was treated with hydrogen in the presence of 20% pd/C to give 0.082 g of 2-aminomethyl-4,8-dimethyl nonanoic acid after filtration and purification via silica gel chromatography (85/15 $CH_2Cl_2$/MeOH). m/z 216.3 (M+).

Example 10

2-Aminomethyl-4,4,8-trimethyl-nonanoic acid 2,2,6-Trimethyl-heptanoic acid methyl ester: To diisopropyl amine (1.54 mL, 11.03 mmol) in THF (22 mL) at −78° C. was added nBuLi (6.89 mL of a 1.6 M solution in hexane). The solution was stirred for 30 min at −78° C., followed by the addition of methyl isobutyrate (0.97 mL, 8.48 mmol). The mixture was stirred at −78° C. for 2 h, and then 1-iodo-4-methyl pentane (1.8 g, 8.48 mmol) and DMPU (0.55 mL, 4.24 mmol) in THF (6 mL) was added. The reaction was stirred at −78° C. and allowed to slowly reach ambient temperature over 16 h. The reaction was quenched by the addition of ammonium chloride (saturated aqueous solution), and the mixture was extracted with EtOAc (2×10 mL). The organics were combined, washed with water, dried (MgSO₄), filtered and concentrated. Silica gel chromatography (99/1 hexane/EtOAc) provided 1.57 g of 2,2,6-Trimethyl-heptanoic acid methyl ester.

2,2,6-Trimethyl-heptan-1-ol: 2,2,6-Trimethyl-heptanoic acid methyl ester (1.97 g, 10.6 mmol) was taken up in toluene (65 mL) and cooled to −78° C. DiBALH (12.7 mL of a 1 N solution in toluene) was added dropwise. After 45 min, 1.5 mL DiBALH was added. After 2 h, the reaction was quenched by the addition of 15 mL MeOH at −78° C. The mixture was warmed to ambient temperature, and then cooled again to −78° C. for the addition of 10 mL 1 N HCl. The mixture was extracted with EtOAc (3×15 mL). The combined organics were washed with brine, dried (MgSO₄), filtered and concentrated. The residual oil was purified via silica gel chromatography (95/5 Hexane/EtOAc) to give 2,2,6-Trimethyl-heptan-1-ol (0.88 g). m/z 159 (M+).

2,2,6-Trimethyl-heptanal: Pyridinium chlorochromate (PCC, 4.17 g, 19.4 mmol) was combined with neutral alumina (14.6 g) in $CH_2Cl_2$ and stirred at ambient temperature for 15 min. The alcohol was diluted in $CH_2Cl_2$, and the mixture was stirred at ambient temperature for 2 h. The solution was filtered through a pad of silica, and the solids were washed with $CH_2Cl_2$. The filtrate was evaporated to give 1.05 g m/z 157 (M+).2,2,6-Trimethyl-heptanal which was carried on without further purification.

2-Cyano-4,4,8-trimethyl-non-2-enoic acid benzyl ester: To a mixture of 2,2,6-Trimethyl-heptanal (1.05 g, 6.73 mmol), piperidine (0.19 mL, 2.01 mmol) and benzyl cyanoacetate (1.29 g, 7.4 mmol) in toluene (50 mL) was added glacial acetic acid (0.72 g, 12.1 mmol). The flask was fitted with a Dean-Stark trap, and the mixture was heated at reflux for 18. The mixture was cooled, treated with dilute HCl, and the layers were separated. The organics were washed with a saturated sodium bicarbonate solution followed by brine, and dried (MgSO$_4$), filtered and concentrated. The residual oil was purified by silica gel chromatography (98/2 hexane/EtOAc) to give 1.3 g of 2-Cyano-4,4,8-trimethyl-non-2-enoic acid benzyl ester m/z 314 (M+).

2-aminomethyl-4,4,8-trimethyl-nonanoic acid: 2-Cyano-4,4,8-trimethyl-non-2-enoic acid benzyl ester (1.3 g, 4.14 mmol) in THF (50 mL) was treated with hydrogen in the presence of 20% Pd/C to give a mixture of the cyano acid and the cyano methyl ester. The mixture was purified by silica gel chromatography to give 278 mg of 80105x41-1-2. The acid was then treated with hydrogen in the presence of Raney Ni in MeOH/NH4OH to give 0.16 g of 2-aminomethyl-4,4,8-trimethyl-nonanoic acid. m/z 230.3 (M+).

Example 11

2-Aminomethyl-4-ethyl-octanoic acid

A procedure similar to that of 2-Aminomethyl-4,4,8-trimethyl-nonanoic acid was utilized to prepare 2-Aminomethyl-4-ethyl-octanoic acid from 2-ethylhexanal. m/z 202.1 (M+).

Example 12

2-Aminomethyl-4-ethyl-8-methyl-nonanoic acid

A procedure similar to that of 2-Aminomethyl-4,4,8-trimethyl-nonanoic acid was utilized to prepare 2-Aminomethyl-8-methyl-nonanoic acid from 2,6-di-t-butyl-4-methylphenyl cyclopropylcarboxylate. m/z 230.2 (M+).

Example 13

3-Amino-2-[1-(4-methyl-pentyl)-cyclopropylmethyl]-propionic acid

A procedure similar to that of 2-Aminomethyl-4,4,8-trimethyl-nonanoic acid was utilized to prepare 2-Aminomethyl-8-methyl-nonanoic acid from 2,6-di-t-butyl-4-methylphenyl cyclopropylcarboxylate. m/z 228.2 (M+).

Example 14

2-Aminomethyl-4-ethyl-hexanoic acid

A procedure similar to 2-aminomethyl-4,8-dimethyl-nonanoic acid was used to prepare 2-aminomethyl-4-ethyl-hexanoic acid from 4-ethyl hexanoic acid. m/z 174.1.

Example 15

3(S)-Amino-3,5-dimethyl-heptanoic acid

2-Methyl-propane-2(S)-sulfinic acid (1,3-dimethyl-pentylidene)-amide: A solution of (S)-(−)-2-methyl-2-propanesulfonamide (500 mg, 4.1 mmol), 4-methyl-2-hexanone (470 mg, 4.1 mmol), and Titanium(IV) ethoxide (1.7 mL, 8.3 mmol) was heated at reflux for 18 h. The reaction mixture was poured into 20 mL brine with rapid stirring. The resulting solution was filtered through celite, and the organic layer was separated. The aqueous layer was extracted with ethyl acetate (2×20 mL). The combined organics were dried (Na$_2$SO$_4$), filtered, and concentrated. The resultant oil was purified by silica gel chromatography (25% EtOAc in hexane) to give 575 mg of 2-Methyl-propane-2(S)-sulfinic acid (1,3-dimethyl-pentylidene)-amide as a yellow oil.

3,5-Dimethyl-3-(2-methyl-propane-2(S)-sulfinylamino)-heptanoic acid methyl ester: To a −78° C. solution of lithium bis(trimethylsilyl)amide (5.1 ml of a 1 M solution in THF) in THF (6 mL) was added methyl acetate ((0.41 mL, 5.1 mmol) dropwise. After stirring for 20 min, a solution of chlorotitanium triisopropoxide (2.5 ml, 10 mmol) in THF (3 mL) was added dropwise. After 1 hour, 2-Methyl-propane-2(S)-sulfinic acid (1,3-dimethyl-pentylidene)-amide (560 mg, 2.6 mmol) in THF (3 mL) was added dropwise at −78° C. The reaction was stirred at −78° C. for 5 h, and then quenched by the addition of 10 mL ammonium chloride solution and warmed to room temperature. The mixture was diluted with 10 mL water, and filtered. The aqueous layer was extracted with ethyl acetate (2×20 mL). The combined organics were washed with brine, dried (Na$_2$SO$_4$), filtered, and concentrated. The resultant oil was purified by silica gel chromatography (30% EtOAc in hexane) to give 360 mg of 3,5-Dimethyl-3-(2-methyl-propane-2(S)-sulfinylamino)-heptanoic acid methyl ester.

3(S)-Amino-3,5-dimethyl-heptanoicacid: 3,5-Dimethyl-3-(2-methyl-propane-2(S)-sulfinylamino)-heptanoic acid methyl ester (360 mg, 1.2 mmol) was dissolved in 6 N HCl (2 mL) and dioxane (2 mL) and heated at 100 C for 6 h. The mixture was cooled to room temperature, diluted with water, and extracted with EtOAc (15 mL). The organics were purified by ion exchange chromatography to give 3(S)-Amino-3,5-dimethyl-heptanoic acid (270 mg) and then repurification by silica gel chromatography (70:25:5 CH$_2$Cl$_2$/MeOH/NH$_4$OH) to give 203 mg of 3(S)-Amino-3,5-dimethyl-heptanoic acid as a white solid. m/z 174 (C$_9$H$_{19}$NO$_2$+H).

Example 16

3(S)-Amino-3,5-dimethyl-nonanoic acid

A procedure similar to that of 3(S)-Amino-3,5-dimethyl-heptanoic acid was used to prepare 3(S)-Amino-3,5-dimethyl-nonanoic acid. m/z 202.1 (C$_{11}$H$_{23}$NO$_2$+H).

Example 17

3(S)-Amino-3,5-dimethyl-octanoic acid

A procedure similar to that of 3(S)-Amino-3,5-dimethyl-heptanoic acid was used to prepare 3(S)-Amino-3,5-dimethyl-nonanoic acid. m/z 188.1 (C$_{10}$H$_{21}$NO$_2$+H).

The invention claimed is:
1. A compound having the formula IA

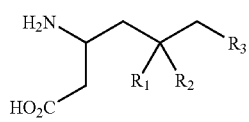

or a pharmaceutically acceptable salt thereof;
wherein $R_1$ is hydrogen or $(C_1–C_3)$alkyl optionally substituted with from one to five fluorine atoms;

$R_2$ is hydrogen or $(C_1-C_3)$alkyl optionally substituted with from one to five fluorine atoms; and $R_3$ is $(C_1-C_6)$alkyl optionally substituted with from one to five fluorine atoms;

with the proviso that when $R_1$ is hydrogen, $R_2$ is not hydrogen.

2. A compound according to claim 1 having the formula IA-1

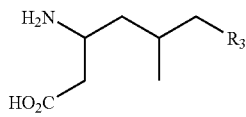

IA-1 or a pharmaceutically acceptable salt thereof;

wherein $R_3$ is $(C_1-C_6)$alkyl optionally substituted with from one to five fluorine atoms.

3. A compound according to claim 1 having the formula IA-2,

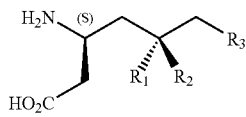

IA-2 or a pharmaceutically acceptable salt thereof;

wherein $R_1$ is hydrogen or $(C_1-C_3)$alkyl optionally substituted with from one to five fluorine atoms;

$R_2$ is hydrogen or $(C_1-C_3)$alkyl optionally substituted with from one to five fluorine atoms; and $R_3$ is $(C_1-C_6)$alkyl optionally substituted with from one to five with the proviso that when $R_1$ is hydrogen, $R_2$ is not hydrogen.

4. A pharmaceutical composition comprising a therapeutically effective amount of a compound according to any of claims 1, 2, and 3, or a pharmaceutically acceptable salt thereof, and a pharmaceutically acceptable carrier.

5. A compound selected from 3-amino-5-methyl-octanoic acid and pharmaceutically acceptable salts thereof.

6. A pharmaceutical composition comprising a therapeutically effective amount of a compound of claim 5 or a pharmaceutically acceptable salt thereof, and a pharmaceutically acceptable carrier.

7. A compound selected from (3S5R)-3-amino-5-methyl-octanoic acid and pharmaceutically acceptable salts thereof.

8. A pharmaceutical composition comprising a therapeutically effective amount of a compound of claim 7 or a pharmaceutically acceptable salt thereof, and a pharmaceutically acceptable carrier.

* * * * *